US006998233B2

(12) United States Patent
Wells et al.

(10) Patent No.: US 6,998,233 B2
(45) Date of Patent: Feb. 14, 2006

(54) METHODS FOR LIGAND DISCOVERY

(75) Inventors: Jim Wells, Burlingame, CA (US); Dan Erlanson, San Francisco, CA (US); Andrew C. Braisted, San Francisco, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 115 days.

(21) Appl. No.: 10/121,216

(22) Filed: Apr. 10, 2002

(65) Prior Publication Data

US 2002/0155505 A1   Oct. 24, 2002

Related U.S. Application Data

(60) Continuation-in-part of application No. 09/981,547, filed on Oct. 17, 2001, which is a division of application No. 09/105,372, filed on Jun. 26, 1998, now Pat. No. 6,335,155, and a continuation-in-part of application No. 09/990,421, filed on Nov. 21, 2001, now Pat. No. 6,919,178.

(60) Provisional application No. 60/252,294, filed on Nov. 21, 2000.

(51) Int. Cl.
  *C12Q 1/68* (2006.01)
(52) U.S. Cl. .......................................... 435/6; 435/7.1
(58) Field of Classification Search ................ 435/6, 435/7.1
  See application file for complete search history.

(56) References Cited

U.S. PATENT DOCUMENTS

| 4,946,778 | A |   | 8/1990  | Ladner et al. ............. 435/69.6 |
| 5,367,058 | A | * | 11/1994 | Pitner et al. ............. 530/391.9 |
| 5,422,281 | A |   | 6/1995  | Harris et al. ................ 436/501 |
| 5,571,681 | A |   | 11/1996 | Janda .......................... 435/7.6 |
| 5,783,384 | A |   | 7/1998  | Verdine ......................... 535/6 |
| 5,958,702 | A |   | 9/1999  | Benner ....................... 435/7.1 |

FOREIGN PATENT DOCUMENTS

| EP | 0 801 307   | 10/1997 |
| WO | WO 95/18972 | 7/1995  |
| WO | WO 95/25737 | 9/1995  |
| WO | WO 96/13613 | 5/1996  |
| WO | WO 96/27605 | 9/1996  |
| WO | WO 97/12897 | 4/1997  |
| WO | WO 97/35202 | 11/1997 |
| WO | WO 97/43302 | 11/1997 |
| WO | WO 98/11436 | 3/1998  |
| WO | WO 98/11437 | 3/1998  |
| WO | WO 98/15969 | 4/1998  |
| WO | WO 98/25146 | 6/1998  |
| WO | WO 98/56028 | 10/1998 |
| WO | WO 98/56028 | 12/1998 |
| WO | WO 99/49314 | 9/1999  |
| WO | WO 99/50668 | 10/1999 |
| WO | WO 99/50669 | 10/1999 |
| WO | WO 99/63944 | 12/1999 |
| WO | WO 00/00823 | 1/2000  |
| WO | WO 00/03240 | 1/2000  |
| WO | WO 01/02856 | 1/2001  |
| WO | WO 02/42773 A2 | 5/2002 |

OTHER PUBLICATIONS

Siuzdak, G. Mass Spectrometry for Biotechnology. New York: Academic Press. 1996, pp. 119-126.*
Marchand-Brynaert, J. et al., "Design and Synthesis of a Bifunctional Label for Selection of β-Lactamase displayed on Filamentous Bacteriophage by Catalytic Activity" *Tetrahedron* 52(15):5591-5606 (1996).
Abraham, D.J. et al., How Allosteric Effectors Can Bind to the Same Protein Residue and Produce Opposite Shifts in the Allosteric Equilibrium *Biochemistry* 34:150006-15020 (1995).
Boyiri, T. et al., "Bisaldehyde Allosteric Effectors as Molecular Ratchets and Probes" *Biochemistry* 34:15021-15036 (1995).
Bunyapaiboonsri et al., "Dynamic Deconvolution of a Pre-Equilibrated Dynamic Combinatorial Library of Acetylcholinesterase Inhibitors" *ChemBioChem* 2:438:444 (2001).
DeJarias et al., "Use of X-ray Co-crystal Structures and Molecular Modeling to Design Potent and Selective Non-peptide Inhibitors of Cathepsin K" *J. Am. Chem. Soc.* 120(35):9114-9115 (1998).
Erlanson et al., "Site-Directed ligand discovery" *PNAS* 97(17):9367-9372 (Aug. 15, 2000).
Hopkins et al., "Suicide Inhibitor of Cytochrome P450 1A1 and P450 2B1" *Biochem. Pharmacol.* 44(4):787-796 (1992).
Huc and Lehn, "Virtual combinatorial libraries: Dynamic generation of molecular and supramolecular diversity by self-assembly" *Proc. Natl. Acad. Sci. USA* 94:2106-2110 (Mar. 1997).
Jones and Thornton, "Principles of protein—protein interactions" *Proc. Natl. Acad. Sci. USA* 93:13-20 (Jan. 1996).
Lehn, Jean-Marie, "Dynamic Combinatorial Chemistry and Virtual Combinatorial Libraries" *Chem. Eur. J.* 5(9)2455-2463 (1999).
Maly et al., "Combinatorial target-guided ligand assembly: identification of potent sybtype-selective c-Src inhibitors" *PNAS* 97(6):2419-2424 (Mar. 14, 2000).
Misumi et al., "The $p^{2gag}$ Peptide, AEAMSQVTNTATIM, Processed for HIC 1 $Pr55^{gag}$ was found to be a Suicide Inhibitor of HIV-1 Protease" *Biochem. Biophys. Res. Commun.* 241(2):275-280 (1997).

(Continued)

*Primary Examiner*—Andrew Wang
*Assistant Examiner*—Jon D. Epperson
(74) *Attorney, Agent, or Firm*—Heller Ehrman LLP

(57) ABSTRACT

The present invention provides novel methods for ligand discovery. The inventive methods rely on a process termed "tethering" where potential ligands are covalently bonded or "tethered" to a target and subsequently identified.

12 Claims, 8 Drawing Sheets

OTHER PUBLICATIONS

Thompson et al., "Design of potent and selective human cathepsin K inhibitors that span the active site", *Proc. Natl. Acad. Sci USA* 94, 14249-14254 (1997).

Feroozesh et al., "Aryl Acetylenes as Mechanism Based Inhibitors of Cytochrome P450-Dependent Mongoxugenase Enzymes" *Chem. Res. Toxicol.* 10(1):91-102 (1997).

Nicolaou et al., "Combinatorial Synthesis Through Disulfide Exchange: Discovery of Potent Psammaplin A Type Antibacterial Agents Active against Methicillin-Resistant Staphylociccus Aureus (MRSA)" *Chem. Eur. J.* 7(19):4280-4295 (2001).

Nicolaou et al., "Synthesis and Biological Evaluation of Vancomycin Dimers with Potent Activity against Vancomycin-Resistant Bacterwria: Target-Accelarated Combinatorial Synthesis" *Chem. Eur. J.* 7(17):2824-2843 (2001).

Pollack, S. J. et al., "introduction of Nucelophines and Spectotroscopic Probes into Antibody Combining Sites" *Science* 242:1038-1040 (1988).

Ramstrom and Lehn, "In Situ Generation and Screening of a Dynamic Combinatorial Carbohydrate Library against Concanavalin A" *ChemBioChem* 1:41-48 (2000).

Sannes-Lowery et al., *Trends Anal. Chem* 19(8):481-491 (2000).

Shuker et al., "Discovering High-Affinity Ligands for Proteins: SAR by NMR" *Science* 274(5292):1531 (Nov. 1996).

Stanojevic and Verdine, "Deconstruction of GCN4/GCRE into a monomeric peptide-DNA complex" *Nature Structural Biology* 2(6):450-457 (Jun. 6, 1995).

Wetterau et al., "An MTP Inhibitor That Normalizes Atherogenic Lipprotein Levels in WHHL Rabbists" *Science* 282:751-754 (Oct. 23, 1998).

Woodcroft et al., "N-Aralkylated derivatives of 1-aminobenzotriazole as isozyme-selective mechanism based inhibitors of guinea pig hepatic cytochrome P-450 dependent monoozygenase activity" *Can J. Physiol. Pharmacol.* 68(9):1278-1285 (1990).

Zhang et al., "Covalent Modification and Active Site-Directed Inactivation of a low Molecular Weight Phosphotyrosyl Protein Phosphatase" *Biochemistry* 31(6): 1701-1711 (1992).

* cited by examiner

METHODS FOR LIGAND DISCOVERY

This application is a continuation-in-part of U.S. Ser. No. 09/981,547 filed Oct. 17, 2001 which is a divisional of U.S. Ser. No. 09/105,372 filed Jun. 26, 1998 now U.S. Pat. No. 6,335,155, and is a continuation-in-part of U.S. Ser. No. 09/990,421 filed Nov. 21, 2001 now U.S. Pat. No. 6,919,178 which asserts priority to U.S. Provisional Application No. 60/252,294 filed Nov. 21, 2000, all of which are incorporated herein by reference.

BACKGROUND

The drug discovery process usually begins with massive functional screening of compound libraries to identify modest affinity leads for subsequent medicinal chemistry optimization. However, not all targets of interest are amenable to such screening. In some cases, an assay that is amenable to high throughput screening is not available. In other cases, the target can have multiple binding modes such that the results of such screens are ambiguous and difficult to interpret. Still in other cases, the assay conditions for high throughput assays are such that they are prone to artifacts. As a result, alternative methods for ligand discovery are needed that do not necessarily rely on functional screens.

DESCRIPTION OF THE FIGURES

FIG. 2A is the deconvoluted mass spectrum of the reaction of thymidylate synthase ("TS") with a pool of 10 different ligand candidates with little or no binding affinity for TS. FIG. 2B is the deconvoluted mass spectrum of the reaction of TS with a pool of 10 different ligand candidates where one of the ligand candidates possesses an inherent binding affinity to the enzyme.

FIG. 3A is the deconvoluted mass spectrum when the reaction is performed without 2-mercaptoethanol. FIG. 3B is the deconvoluted mass spectrum when the same reaction is in the presence of 0.2 mM 2-mercaptoethanol. FIG. 3C is the deconvoluted mass spectrum when the same reaction is in the presence of 20 mM 2-mercaptoethanol.

FIG. 4A is a tethering experiment with a library pool comprising 20 ligand candidates. FIG. 4B is a tethering experiment with a library pool comprising 50 ligand candidates. FIG. 4C is a tethering experiment with a library pool comprising 100 ligand candidates.

SUMMARY OF THE INVENTION

Figure 1:
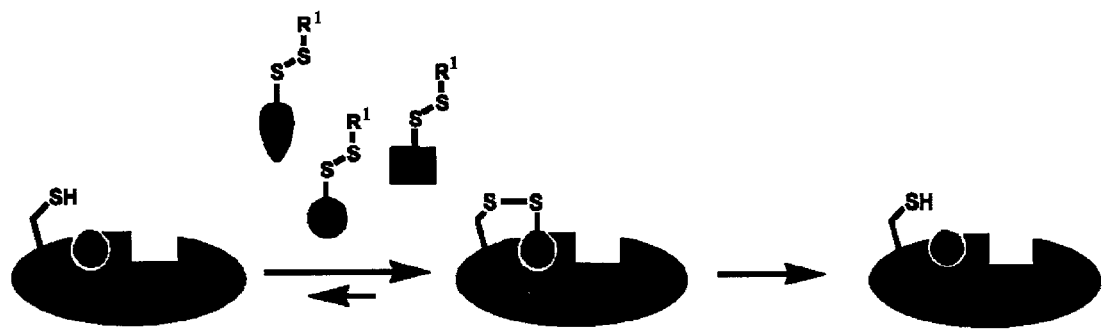
FIG. 1A is a schematic illustration of one embodiment of the tethering method. A thiol-containing protein is reacted with a plurality of ligand candidates. A ligand candidate that possesses an inherent binding affinity for the target is identified and a ligand is made comprising the identified binding determinant (represented by the circle) that does not include the disulfide moiety.
FIG. 1B is a schematic representation of the theory behind tethering. When a thiol-containing protein is equilibrated with at least one disulfide-containing ligand candidate, most preferably in the presence of a reducing agent, equilibrium between the modified and unmodified protein is established. If the ligand candidate does not have an inherent binding affinity for the target protein, the equilibrium is shifted toward the unmodified protein. In contrast, if the ligand candidate does have an inherent affinity for the protein, the equilibrium shifts toward the modified protein.
Figure 1:
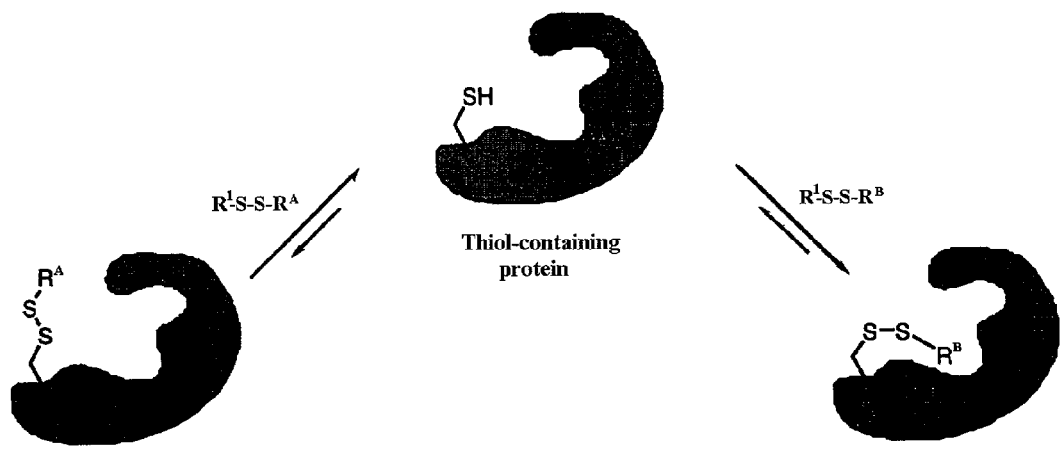

The invention concerns methods for ligand discovery using tethering technology.

In one aspect, the invention concerns a method comprising
a) contacting a target that comprises a chemically reactive group at or near a site of interest with a compound that is capable of forming a covalent bond with the chemically reactive group;
b) forming a covalent bond between the target and the compound thereby forming a target-compound conjugate; and,
c) identifying the target-compound conjugate by subjecting the target-compound conjugate to mass spectrometry.

In another aspect, the invention concerns a mass spectrometer comprising a target-compound conjugate.

In a further aspect, the invention concerns a target-compound conjugate selected from the group consisting of

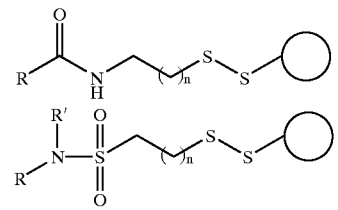

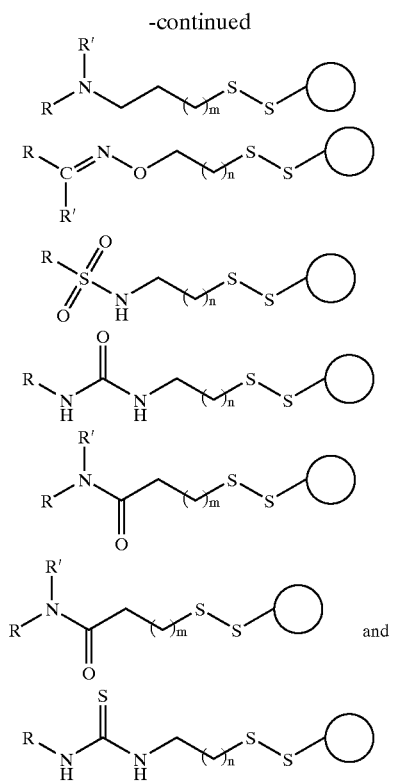

wherein

is the target, R and R' are each independently unsubstituted $C_1$–$C_{20}$ aliphatic, substituted $C_1$–$C_{20}$ aliphatic, unsubstituted aryl, or substituted aryl;

m is 0, 1, or 2; and, n is 1 or 2.

In a particular embodiment, the target is a polypeptide or a protein, which may, for example, be selected from the group consisting of enzymes, receptors, transcription factors, ligands for receptors, growth factors, cytokines, immunoglobulins, nuclear proteins, signal transduction components, and allosteric enzyme regulators. The covalent bond between the —S—S— bond and the target compound may be reversible or irreversible.

In yet another aspect, the invention concerns a method comprising:

a) contacting a target protein that is capable of forming a disulfide bond with a ligand candidate that is also capable of forming a disulfide bond;

b) forming a disulfide bond between the target protein and the ligand candidate thereby forming a target-ligand conjugate; and c) identifying the ligand present in the target protein-ligand conjugate.

In certain embodiments, the contacting step occurs in the presence of a reducing agent. In another embodiment, the identification step may be performed using mass spectrometry. In yet another embodiment, the identification may be performed using a labeled probe. In a still further embodiments, the identification step is performed using a functional assay, chromatography, or surface plasmon resonance.

In a specific embodiment of the method described above, the ligand candidate is selected from the group comprising

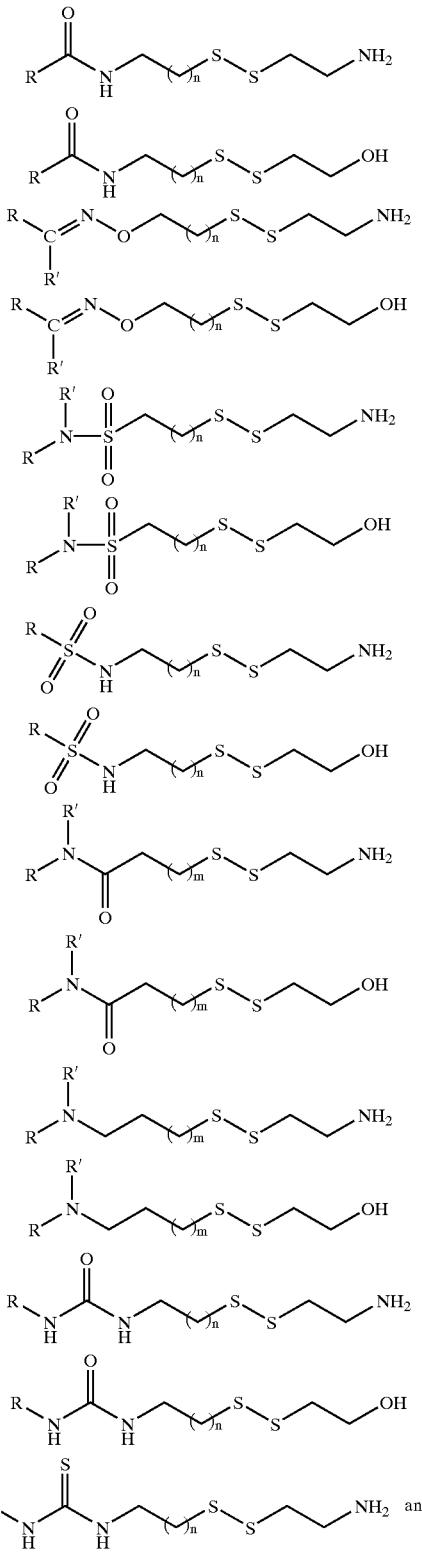

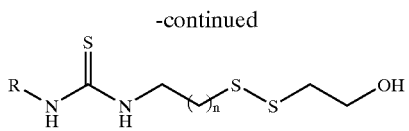

wherein R and R' are each independently unsubstituted $C_1-C_{20}$ aliphatic, substituted $C_1-C_{20}$ aliphatic, unsubstituted aryl, or substituted aryl;

m is 0, 1, or 2; and, n is 1 or 2.

The target protein may comprise an —SH group that is from a cysteine which is part of the native amino acid sequence of the protein, or may be from a cysteine that is introduced into the native amino acid sequence of the protein.

In another aspect, the invention concerns a library of compounds wherein each member comprises a moiety —SSR$^1$ where R$^1$ is unsubstituted $C_1-C_{10}$ aliphatic, substituted $C_1-C_{10}$ aliphatic, unsubstituted aryl, and wherein each member has a different mass. The library preferably has at least about 5 members, more preferably at least about 100 members, and the atomic mass of the individual members of the library preferably differs by at least about 5 atomic mass units, more preferably by at least about 10 atomic mass units.

In a further aspect, the invention concerns a method comprising:

a) identifying a first compound of the formula R$^D$SSR$^1$ that binds to a target protein;

b) identifying a second compound of the formula R$^E$SSR$^1$ that binds to a target protein; and c) forming a conjugate compound comprising R$^D$ and R$^E$ wherein R$^D$ and R$^E$ are each independently $C_1-C_{20}$ unsubstituted aliphatic, $C_1-C_{20}$ substituted aliphatic, unsubstituted aryl, and substituted aryl; and R$^1$ is unsubstituted $C_1-C_{10}$ aliphatic, substituted $C_1-C_{10}$ aliphatic, unsubstituted aryl. In a particular embodiment of this method, the identification of the second compound that binds to the target occurs in the presence of the first compound.

In another embodiment, R$^D$SSR$^1$ and R$^E$SSR$^1$ are each independently selected from the group consisting of

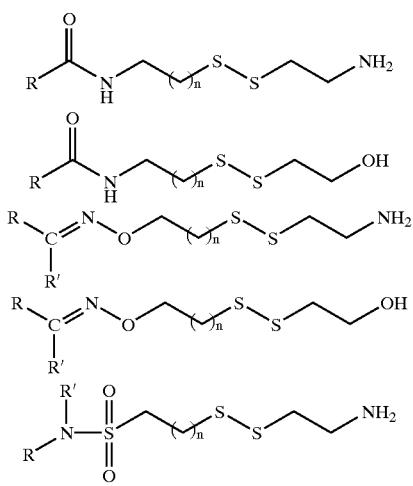

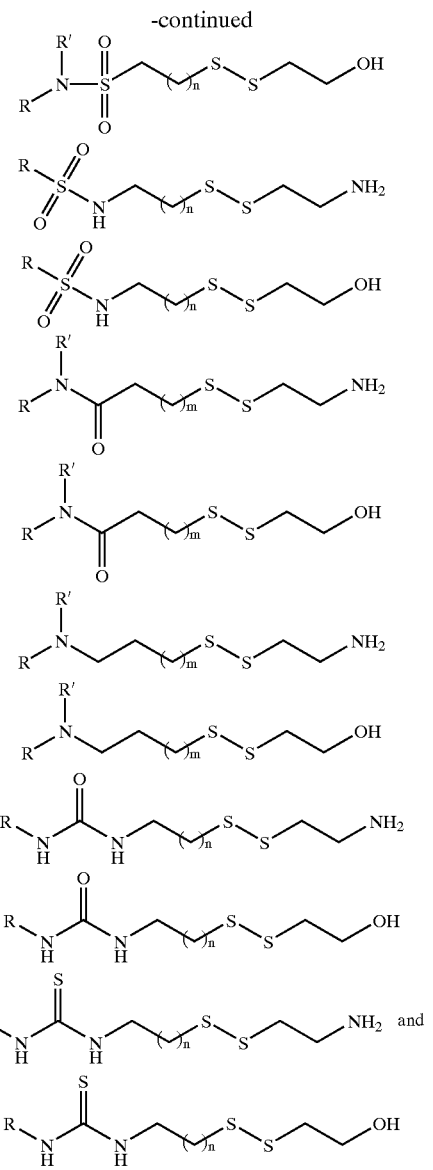

wherein R and R' are each independently unsubstituted $C_1-C_{20}$ aliphatic, substituted $C_1-C_{20}$ aliphatic, unsubstituted aryl, or substituted aryl;

m is 0, 1, or 2; and, n is 1 or 2.

In a still further aspect, the invention concerns a method comprising a) providing a target having an anchoring group that is capable of forming a covalent bond or coordinating a metal at or near a site of interest;

b) contacting the target with an extender thereby forming a target-extender complex wherein the extender comprises a first functionality that forms either a covalent bond or coordinates a metal and a second functionality that is capable of forming a covalent bond;

c) contacting the target-extender complex with a candidate ligand that comprises a group that is capable of forming a covalent bond with the second functionality;

d) forming a covalent bond between the target-extender complex and the candidate ligand; and, e) identifying the candidate ligand present in the target-extender-ligand conjugate.

In specific embodiments of this method, the anchoring group is selected from a group consisting of a reactive electrophile, a reactive nucleophile, and a metal coordination site.

The invention also relates to a method comprising:

a) providing a target having a reactive nucleophile at or near a site of interest;
b) contacting the target with an extender thereby forming a target-extender complex wherein the extender comprises a first functionality that reacts with the nucleophile in the target to form a covalent bond and a second functionality that is capable of forming a disulfide bond;
c) contacting the target-extender complex with a ligand candidate that is capable of forming a disulfide bond;
d) forming a disulfide bond between the target-extender complex and the ligand candidate thereby forming a target-extender-ligand conjugate; and,
e) identifying the ligand candidate present in the target-extender-ligand conjugate.

The reactive nucleophile on the target may, for example, be a thiol or a masked thiol, and the extender may has the formula:

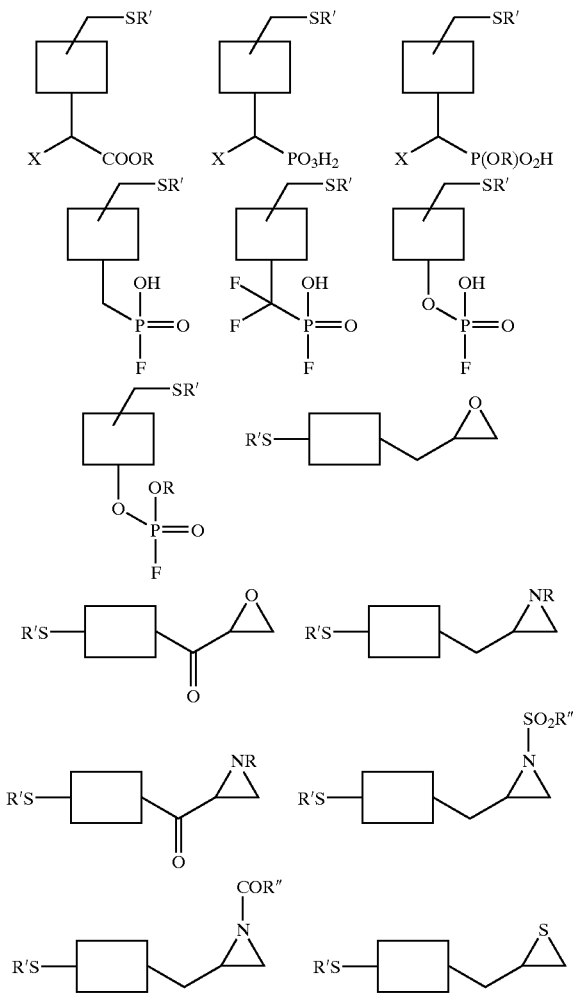

-continued

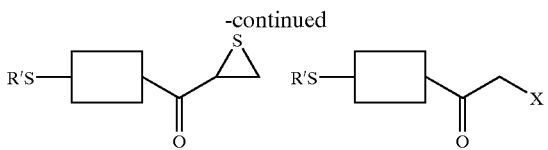

where R is unsubstituted $C_1$–$C_{20}$ aliphatic, substituted $C_1$–$C_{20}$ aliphatic, unsubstituted aryl, and substituted aryl; R' is H, —$SR^1$ wherein $R^1$ is unsubstituted $C_1$–$C_{10}$ aliphatic, substituted $C_1$–$C_{10}$ aliphatic, unsubstituted aryl, and substituted aryl; X is a leaving group, and the boxes in each formula represent a binding determinant.

In a specific embodiment, the extender is of the formula:

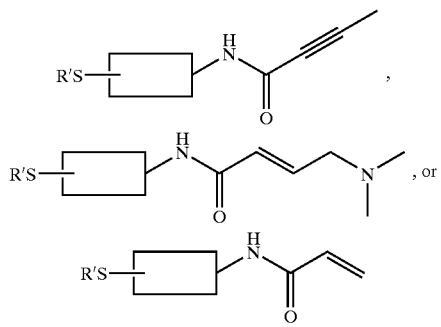

where R' is H, —$SR^1$ wherein $R^1$ is unsubstituted $C_1$–$C_{10}$ aliphatic, substituted $C_1$–$C_{10}$ aliphatic, unsubstituted aryl, and substituted aryl, and the boxes represent a binding determinant.

In a different aspect, the invention concerns a protein-extender complex wherein the protein forms a covalent bond with an extender comprising a first functionality that is capable of forming a covalent bond and a second functionality that is capable of forming a second covalent bond.

In another aspect, the invention concerns a protein-extender complex wherein the protein coordinates a metal with an extender comprising a first functionality that is capable of coordinating a metal and a second functionality that is capable of forming a covalent bond.

The complexes may further comprise a disulfide bond between the second functionality and a compound that is capable of forming a disulfide bond.

DESCRIPTION OF THE PREFERRED EMBODIMENTS

The present invention provides a rapid and efficient method for identifying ligands that are capable of binding to selected sites on targets of interest. The ligands themselves identified by the methods herein find use, for example, as lead compounds for the development of novel therapeutic drugs, enzyme inhibitors, labeling compounds, diagnostic reagents, affinity reagents for protein purification, and the like.

Unless defined otherwise, technical and scientific terms used herein have the same meaning as commonly understood by one of ordinary skill in the art to which this invention belongs. References, such as Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

In one aspect of the present invention, compounds are provided. Unless explicitly or implicitly indicated otherwise, these compounds can be in the form of an individual enantiomer, diasteromer, geometric isomer, or mixtures thereof. In the case of compounds containing double bonds, these double bonds can be either Z or E or a mixture thereof, unless otherwise indicated.

Definitions

The definition of terms used herein include:

The term "aliphatic" or "unsubstituted aliphatic" refers to a straight, branched, cyclic, or polycyclic hydrocarbon and includes alkyl, alkenyl, alkynyl, cycloalkyl, cycloalkenyl, and cycloalkynyl moieties.

The term "alkyl" or "unsubstituted alkyl" refers to a saturated hydrocarbon.

The term "alkenyl" or "unsubstituted alkenyl" refers to a hydrocarbon with at least one carbon-carbon double bond.

The term "alkynyl" or "unsubstituted alkynyl" refers to a hydrocarbon with at least one carbon-carbon triple bond.

The term "aryl" or "unsubstituted aryl" refers to mono or polycyclic unsaturated moieties having at least one aromatic ring. The term includes heteroaryls that include one or more heteroatoms within the at least one aromatic ring. Illustrative examples of aryl include: phenyl, naphthyl, tetrahydronaphthyl, indanyl, indenyl, pyridyl, pyrazinyl, pyrimidinyl, pyrrolyl, pyrazolyl, imidazolyl, thiazolyl, oxazolyl, isooxazoly, thiadiazolyl, oxadiazolyl, thiophenyl, furanyl, quinolinyl, isoquinolinyl, and the like.

The term "substituted" when used to modify a moiety refers to a substituted version of the moiety where at least one hydrogen atom is substituted with another group including but not limited to: aliphatic; aryl, alkylaryl, F, Cl, I, Br, —OH; —NO$_2$; —CN; —CF$_3$; —CH$_2$CF$_3$; —CH$_2$Cl; —CH$_2$OH; —CH$_2$CH$_2$OH; —CH$_2$NH$_2$; —CH$_2$SO$_2$CH$_3$; —OR$^x$; —C(O)R$^x$; —COOR$^x$; —C(O)N(R$^x$)$_2$; —OC(O)R$^x$; —OCOOR$^x$; —OC(O)N(R$^x$)$_2$; —N(R$^x$)$_2$; —S(O)$_2$R$^x$; and —NR$^x$C(O)R$^x$ where each occurrence of R$^x$ is independently hydrogen, substituted aliphatic, unsubstituted aliphatic, substituted aryl, or unsubstituted aryl. Additionally, substitutions at adjacent groups on a moiety can together form a cyclic group.

The term "antagonist" is used in the broadest sense and includes any ligand that partially or fully blocks, inhibits or neutralizes a biological activity exhibited by a target, such as a TBM. In a similar manner, the term "agonist" is used in the broadest sense and includes any ligand that mimics a biological activity exhibited by a target, such as a TBM, for example, by specifically changing the function or expression of such TBM, or the efficiency of signaling through such TBM, thereby altering (increasing or inhibiting) an already existing biological activity or triggering a new biological activity.

The term "extender" refers to a molecule having a molecular weight of from about 30 to about 1,500 daltons and having a first functional group that is capable of reacting with group on a target and a second functional group that is capable of reacting with a ligand candidate or members of a library of ligand candidates to form a disulfide bond.

The term "ligand" refers to an entity that possesses a measurable binding affinity for the target. In general, a ligand is said to have a measurable affinity if it binds to the target with a $K_d$ or a $K_i$ of less than about 100 mM, preferably less than about 10 mM, and more preferably less than about 1 mM. In preferred embodiments, the ligand is not a peptide and is a small molecule. A ligand is a small molecule if it is less than about 2000 daltons in size, usually less than about 1500 daltons in size. In more preferred embodiments, the small molecule ligand is less than about 1000 daltons in size, usually less than about 750 daltons in size, and more usually less than about 500 daltons in size.

The term "binding determinant" with reference to an extender relates to a portion of the extender that participates in binding to a target, such as a target polypeptide.

The term "ligand candidate" refers to a compound that possesses or has been modified to possess a reactive group that is capable of forming a covalent bond with a complimentary or compatible reactive group on a target. The reactive group on either the ligand candidate or the target can be masked with, for example, a protecting group.

The term "polynucleotide", when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The phrase "protected thiol" as used herein refers to a thiol that has been reacted with a group or molecule to form a covalent bond that renders it less reactive and which may be deprotected to regenerate a free thiol.

The phrase "reversible covalent bond" as used herein refers to a covalent bond that can be broken, preferably under conditions that do not denature the target. Examples include, without limitation, disulfides, Schiff-bases, thioesters, coordination complexes, boronate esters, and the like.

The phrase "reactive group" is a chemical group or moiety providing a site at which a covalent bond can be made when presented with a compatible or complementary reactive group. Illustrative examples are —SH that can react with another —SH or —SS— to form a disulfide; an —NH$_2$ that can react with an activated —COOH to form an amide; an —NH$_2$ that can react with an aldehyde or ketone to form a Schiff base and the like.

The phrase "reactive nucleophile" as used herein refers to a nucleophile that is capable of forming a covalent bond with a compatible functional group on another molecule under conditions that do not denature or damage the target. The most relevant nucleophiles are thiols, alcohols, and amines. Similarly, the phrase "reactive electrophile" as used herein refers to an electrophile that is capable of forming a covalent bond with a compatible functional group on another molecule, preferably under conditions that do not denature or otherwise damage the target. The most relevant electrophiles are imines, carbonyls, epoxides, aziridies, sulfonates, disulfides, activated esters, activated carbonyls, and hemiacetals.

The phrase "site of interest" refers to any site on a target on which a ligand can bind. For example, when the target is an enzyme, the site of interest can include amino acids that make contact with, or lie within about 10 Angstroms (more preferably within about 5 Angstroms) of a bound substrate, inhibitor, activator, cofactor, or allosteric modulator of the enzyme. When the enzyme is a protease, the site of interest includes the substrate binding channel from P6 to P6', residues involved in catalytic function (e.g. the catalytic triad and oxy anion hole), and any cofactor (e.g. metal such as Zn) binding site. When the enzyme is a protein kinase, the site of interest includes the substrate-binding channel in addition to the ATP binding site. When the enzyme is a dehydrogenease, the site of interest includes the substrate binding region as well as the site occupied by NAD/NADH. When the enzyme is a hydralase such as PDE4, the site of interest includes the residues in contact with cAMP as well as the residues involved in the binding of the catalytic divalent cations.

The terms "target," "Target Molecule," and "TM" are used interchangeably and in the broadest sense, and refer to a chemical or biological entity for which the binding of a ligand has an effect on the function of the target. The target can be a molecule, a portion of a molecule, or an aggregate of molecules. The binding of a ligand may be reversible or irreversible. Specific examples of target molecules include polypeptides or proteins (e.g., enzymes, including proteases, e.g. cysteine, serine, and aspartyl proteases), receptors, transcription factors, ligands for receptors, growth factors, cytokines, immunoglobulins, nuclear proteins, signal transduction components (e.g., kinases, phosphatases), allosteric enzyme regulators, and the like, polynucleotides, peptides, carbohydrates, glycoproteins, glycolipids, and other macromolecules, such as nucleic acid-protein complexes, chromatin or ribosomes, lipid bilayer-containing structures, such as membranes, or structures derived from membranes, such as vesicles. The definition specifically includes Target Biological Molecules ("TBMs") as defined below.

A "Target Biological Molecule" or "TBM" as used herein refers to a single biological molecule or a plurality of biological molecules capable of forming a biologically relevant complex with one another for which a small molecule agonist or antagonist has an effect on the function of the TBM. In a preferred embodiment, the TBM is a protein or a portion thereof or that comprises two or more amino acids, and which possesses or is capable of being modified to possess a reactive group that is capable of forming a covalent bond with a compound having a complementary reactive group. Illustrative examples of TBMs include: enzymes, receptors, transcription factors, ligands for receptors, growth factors, immunoglobulins, nuclear proteins, signal transduction components, glycoproteins, glycolipids, and other macromolecules, such as nucleic acid-protein complexes, chromatin or ribosomes, lipid bilayer-containing structures, such as membranes, or structures derived from membranes, such as vesicles. The target can be obtained in a variety of ways, including isolation and purification from natural source, chemical synthesis, recombinant production and any combination of these and similar methods.

Preferred protein targets include: cell surface and soluble receptor proteins, such as lymphocyte cell surface receptors; enzymes; proteases (e.g., aspartyl, cysteine, metallo, and serine); steroid receptors; nuclear proteins; allosteric enzymes; clotting factors; kinases (serine/threonine kinases and tyrosine kinases); phosphatases (serine/threonine, tyrosine, and dual specificity phosphatases, especially PTP-1B, TC-PTP and LAR); thymidylate synthase; bacterial enzymes, fungal enzymes and viral enzymes (especially those associated with HIV, influenza, rhinovirus and RSV); signal transduction molecules; transcription factors; proteins or enzymes associated with DNA and/or RNA synthesis or degradation; immunoglobulins; hormones; and receptors for various cytokines. Illustrative examples of receptors include for example, erythropoietin (EPO), granulocyte colony stimulating (G-CSF) receptor, granulocyte macrophage colony stimulating (GM-CSF) receptor, thrombopoietin (TPO), interleukins, e.g. IL-2, IL-3, IL-4, IL-5, IL-6, IL-10, IL-11, IL-12, growth hormone, prolactin, human placental lactogen (LPL), CNTF, oncostatin, RANTES, MIPb, IL-8, insulin, insulin-like growth factor 1 (IGF-1), epidermal growth factor (EGF), heregulin-a and heregulin-b, vascular endothelial growth factor (VEGF), placental growth factor (PLGF), tissue growth factors (TGF-α and TGF-β), and nerve growth factor (NGF). Other targets include various neurotrophins and their ligands, other hormones and receptors such as, bone morphogenic factors, follicle stimulating hormone (FSH), and luteinizing hormone (LH), CD40 ligand, apoptosis factor-1 and -2 (AP-1 and AP-2), p53, bax/bcl2, mdm2, caspases (1, 3, 8 and 9), cathepsins, IL-1/IL-1 receptor, BACE, HIV integrase, PDE IV, Hepatitis C helicase, Hepatitis C protease, rhinovirus protease, tryptase, cPLA (cytosolic Phospholipase A2), CDK4, c-jun kinase, adaptors such as Grb2, GSK-3, AKT, MEKK-1, PAK-1, raf, TRAF's 1–6, Tie2, ErbB 1 and 2, FGF, PDGF, PARP, CD2, C5a receptor, CD4, CD26, CD3, TGF-alpha, NF-kB, IKK beta, STAT 6, Neurokinnin-1, CD45, Cdc25A, SHIP-2, human p53, bax/bcl2, IgE/IgER, ZAP-70, lck, syk, ITK/BTK, TACE, Cathepsin S, K and F, CD11a, LFA/ICAM, VLA-4, CD28/B7, CTLA4, TNF alpha and beta, (and the p55 and p75 TNF receptors), CD40L, p38 map kinase, IL-2, IL-4, Il-13, IL-15, Rac 2, PKC theta, IL-8, TAK-1, jnk, IKK2 and IL-18.

The Tethering Method

The present invention provides novel methods for ligand discovery that rely on a process termed "tethering." Potential ligands are covalently bonded or "tethered" to a target and subsequently identified. As noted before, in one aspect of the present invention, the method comprises:

a) contacting a target that comprises a chemically reactive group at or near a site of interest with a compound that is capable of forming a covalent bond with the chemically reactive group;

b) forming a covalent bond between the target and the compound thereby forming a target-compound conjugate; and, c) identifying the target-compound conjugate.

In one embodiment, a plurality of compounds are used so that the method comprises:

a) obtaining a target that comprises a chemically reactive group at or near a site of interest;

b) combining the target with a plurality of compounds that are capable of covalently bonding to the chemically reactive group and wherein at least one compound forms a covalent bond with the target; and, c) identifying the compound that formed the covalent bond in the target-compound conjugate.

In preferred embodiments, the target is a protein and the chemically reactive group is a thiol on a cysteine residue therein. If a site of interest does not include a naturally occurring cysteine residue, then the target can be modified to include a cysteine residue at or near the site of interest. A cysteine is said to be near the site of interest if it is located within 10 Angstroms from the site of interest, preferably within 5 Ångstroms from the site of interest. Preferred residues for modification are those that are solvent-accessible. Solvent accessibility may be calculated from structural models using standard numeric (Lee, B. & Richards, F. M. *J. Mol. Biol* 55:379–400 (1971); Shrake, A. & Rupley, J. A. *J. Mol. Biol.* 79:351–371 (1973)) or analytical (Connolly, M. L. *Science* 221:709–713 (1983); Richmond, T. J. *J. Mol. Biol.* 178:63–89 (1984)) methods. For example, a potential cysteine variant is considered solvent-accessible if the combined surface area of the carbon-beta (CB), or sulfur-gamma (SG) is greater than 21 $Å^2$ when calculated by the method of Lee and Richards (Lee, B. & Richards, F. M. *J. Mol. Biol* 55:379–400 (1971)). This value represents approximately 33% of the theoretical surface area accessible to a cysteine side-chain as described by Creamer et al. (Creamer, T. P. et al. *Biochemistry* 34:16245–16250 (1995)).

It is also preferred that the residue to be mutated to cysteine, or another thiol-containing amino acid residue, not participate in hydrogen-bonding with backbone atoms or, that at most, it interacts with the backbone through only one hydrogen bond. Wild-type residues where the side-chain participates in multiple (>1) hydrogen bonds with other side-chains are also less preferred. Variants for which all standard rotamers (chi1 angle of −60°, 60°, or 180°) can introduce unfavorable steric contacts with the N, CA, C, O, or CB atoms of any other residue are also less preferred. Unfavorable contacts are defined as interatomic distances that are less than 80% of the sum of the van der Waals radii of the participating atoms. In certain embodiments where the site of interest is a concave region, residues found at the edge of such a site (such as a ridge or an adjacent convex region) are more preferred for mutating into cysteine residues. Convexity and concavity can be calculated based on surface vectors (Duncan, B. S. & Olson, A. J. *Biopolymers* 33:219–229 (1993)) or by determining the accessibility of water probes placed along the molecular surface (Nicholls, A. et al. *Proteins* 11:281–296 (1991); Brady, G. P., Jr. & Stouten, P. F. *J. Comput. Aided Mol. Des.* 14:383–401 (2000)). Residues possessing a backbone conformation that is nominally forbidden for L-amino acids (Ramachandran, G. N. et al. *J. Mol. Biol.* 7:95–99 (1963); Ramachandran, G. N. & Sasisekharahn, V. *Adv. Prot. Chem.* 23:283–437 (1968)) are less preferred targets for modification to a cysteine. Forbidden conformations commonly feature a positive value of the phi angle.

Other preferred variants are those which, when mutated to cysteine and tethered as to comprise -Cys-SSR$^1$, would possess a conformation that directs the atoms of $R^1$ towards the site of interest. Two general procedures can be used to identify these preferred variants. In the first procedure, a search is made of unique structures (Hobohm, U. et al. *Protein Science* 1:409–417 (1992)) in the Protein Databank (Berman, H. M. et al. *Nucleic Acids Research* 28:235–242 (2000)) to identify structural fragments containing a disulfide-bonded cysteine at position j in which the backbone atoms of residues j−1, j, and j+1 of the fragment can be superimposed on the backbone atoms of residues i−1, i, and i+1 of the target molecule with an RMSD of less than 0.75 squared Angstroms. If fragments are identified that place the C β atom of the residue disulfide-bonded to the cysteine at position j closer to any atom of the site of interest than the C β atom of residue i (when mutated to cysteine), position i is considered preferred. In an alternative procedure, the residue at position i is computationally "mutated" to a cysteine and capped with an S-Methyl group via a disulfide bond.

In addition to adding one or more cysteines to a site of interest, it may be desirable to delete one or more naturally occurring cysteines (and replacing them with alanines for example) that are located outside of the site of interest. These mutants wherein one or more naturally occurring cysteines are deleted or "scrubbed" comprise another aspect of the present invention. Various recombinant, chemical, synthesis and/or other techniques can be employed to modify a target such that it possesses a desired number of free thiol groups that are available for tethering. Such techniques include, for example, site-directed mutagenesis of the nucleic acid sequence encoding the target polypeptide such that it encodes a polypeptide with a different number of cysteine residues. Particularly preferred is site-directed mutagenesis using polymerase chain reaction (PCR) amplification (see, for example, U.S. Pat. No. 4,683,195 issued 28, Jul. 1987; and Current Protocols In Molecular Biology, Chapter 15 (Ausubel et al., ed., 1991). Other site-directed mutagenesis techniques are also well known in the art and are described, for example, in the following publications: Ausubel et al., supra, Chapter 8; Molecular Cloning: A Laboratory Manual., 2nd edition (Sambrook et al., 1989); Zoller et al., Methods Enzymol. 100:468–500 (1983); Zoller & Smith, DNA 3:479–488 (1984); Zoller et al., Nucl. Acids Res., 10:6487 (1987); Brake et al., Proc. Natl. Acad. Sci. USA 81:4642–4646 (1984); Botstein et al., Science 229: 1193 (1985); Kunkel et al., Methods Enzymol. 154:367–82 (1987), Adelman et al., DNA 2:183 (1983); and Carter et al., Nucl. Acids Res., 13:4331 (1986). Cassette mutagenesis (Wells et al., Gene, 34:315 [1985]), and restriction selection mutagenesis (Wells et al., Philos. Trans. R. Soc. London SerA, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Once the target-compound conjugate is formed, it can be detected using a number of methods. In one embodiment, mass spectroscopy is used. The target-compound conjugate can be detected directly in the mass spectroscopy or the target compound conjugate can be fragmented prior to detection. Alternatively, the compound can be liberated within the mass spectrophotometer and subsequently identified. As described in greater detail below, the use of mass spectrometry to identify the compound in a target-compound conjugate in such a facile and robust manner is one of the surprising and unexpected findings of the present invention. Both the target-compound conjugate and a mass spectrometer (MS) comprising a target-compound conjugate comprise aspects of the present invention.

MS detects molecules based on mass-to-charge ratio (m/z) and thus can resolve molecules based on their sizes (reviewed in Yates, *Trends Genet.* 16: 5–8 [2000]). A mass spectrometer first converts molecules into gas-phase ions, then individual ions are separated on the basis of m/z ratios and are finally detected. A mass analyzer, which is an integral part of a mass spectrometer, uses a physical property (e.g. electric or magnetic fields, or time-of-flight [TOF]) to separate ions of a particular m/z value that then strikes the ion detector. Mass spectrometers are capable of generating data quickly and thus have a great potential for high-throughput analysis. Mass spectroscopy may be employed either alone or in combination with other means for detection or identifying the compounds covalently bound to the target. Further descriptions of mass spectroscopy techniques include Fitzgerald and Siuzdak, *Chemistry & Biology* 3: 707–715 [1996]; Chu et al., *J. Am. Chem. Soc.* 118: 7827–7835 [1996]; Siudzak, *Proc. Natl. Acad. Sci. USA* 91: 11290–11297 [1994]; Burlingame et al, *Anal. Chem.* 68: 599R–651R [1996]; Wu et al., *Chemistry & Biology* 4: 653–657 [1997]; and Loo et al., *Am. Reports Med. Chem.* 31: 319–325 [1996]).

The target-compound conjugate can be identified using other means. For example, one can employ various chromatographic techniques such as liquid chromatography, thin layer chromatography and the like for separation of the components of the reaction mixture so as to enhance the ability to identify the covalently bound molecule. Such chromatographic techniques can be employed in combination with mass spectroscopy or separate from mass spectroscopy. One can also couple a labeled probe (fluorescently, radioactively, or otherwise) to the liberated compound so as to facilitate its identification using any of the above techniques. In yet another embodiment, the formation of the new bonds liberates a labeled probe, which can then be monitored. A simple functional assay, such as an ELISA or enzymatic assay can also be used to detect binding when binding occurs in an area essential for what the assay measures. Other techniques that may find use for identifying the organic compound bound to the target molecule include, for example, nuclear magnetic resonance (NMR), surface plasmon resonance (e.g., BIACORE), capillary electrophoresis, X-ray crystallography, and the like, all of which will be well known to those skilled in the art.

In another aspect of the present invention, the target is a protein and the covalent bond or tether is a disulfide bond. The method comprises:
a) contacting a target protein that is capable of forming a disulfide bond with a ligand candidate that is also capable of forming a disulfide bond;
b) forming a disulfide bond between the target protein and the ligand candidate thereby forming a target protein-ligand conjugate; and
c) identifying the ligand present in the target protein-ligand conjugate.

Optionally, the target protein is contacted with a ligand candidate in the presence of a reducing agent. Illustrative examples of suitable reducing agents include but are not limited to: cysteine, cysteamine, dithiothreitol, dithioerythritol, glutathione, 2-mercaptoethanol, 3-mercaptoproprionic acid, a phosphine such as tris-(2-carboxyethyl-phosphine) ("TCEP"), or sodium borohydride. In one embodiment, the reducing agent is 2-mercaptoethanol. In another embodiment, the reducing agent is cysteamine. In another embodiment, the reducing agent is glutathione. In another embodiment, the reducing agent is cysteine.

In one embodiment, the target protein possesses a naturally occurring —SH group from a cysteine that is part of the naturally occurring protein sequence. In another embodiment, the target protein possesses an engineered —SH group where mutagenesis was used to mutate a naturally occurring amino acid to a cysteine. These target proteins with non-native cysteines comprise another aspect of the present invention.

In another embodiment, the target protein possesses a masked —SH in the form of a disulfide. In another embodiment, the target protein possesses a cysteine where the thiol is masked as a disulfide. In another embodiment, the target protein possesses a cysteine where the thiol forms a disulfide bond with another cysteine. In another embodiment, the target protein possesses a cysteine where the thiol forms a disulfide bond with glutathione. In another embodiment, the target protein possesses a cysteine where the thiol forms a disulfide of the formula —SSR$^1$ where R$^1$ is unsubstituted C$_1$–C$_{10}$ aliphatic, substituted C$_1$–C$_{10}$ aliphatic unsubstituted aryl or substituted aryl. In another embodiment, the target protein possesses a cysteine where the thiol is masked as a disulfide of the formula —SSR$^2$R$^3$ wherein R$^2$ is C$_1$–C$_5$ alkyl and R$^3$ is NH$_2$, OH, or COOH. In another embodiment, the target protein possesses a cysteine where the thiol is masked as a disulfide of the formula —SSCH$_2$CH$_2$OH. In yet another embodiment, the target protein possesses a cysteine where the thiol is masked as a disulfide of the formula —SSCH$_2$CH$_2$NH$_2$.

In another embodiment, the ligand candidate possesses a —SH group. In another embodiment, the ligand candidate possesses a masked thiol. The ligand candidates with masked thiol groups comprise another aspect of the present invention. In another embodiment, the ligand candidate possesses a masked thiol in the form of a disulfide of the formula —SSR$^1$ where R$^1$ is unsubstituted C$_1$–C$_{10}$ aliphatic, substituted C$_1$–C$_{10}$ aliphatic, unsubstituted aryl or substituted aryl. In another embodiment, the ligand candidate possesses a thiol masked as a disulfide of the formula —SSR$^2$R$^3$ wherein R$^2$ is C$_1$–C$_5$ alkyl (preferably —CH$_2$—, —CH$_2$CH$_2$—, or —CH$_2$CH$_2$CH$_2$—) and R$^3$ is NH$_2$, OH, or COOH. In another embodiment, the ligand candidate possesses a thiol masked as a disulfide of the formula —SSCH$_2$CH$_2$OH. In yet another embodiment, the ligand candidate possesses a thiol masked as a disulfide of the formula —SSCH$_2$CH$_2$NH$_2$. Illustrative examples of ligand candidates include:

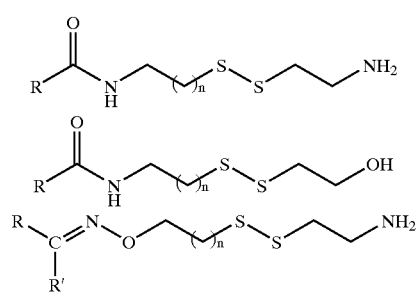

-continued

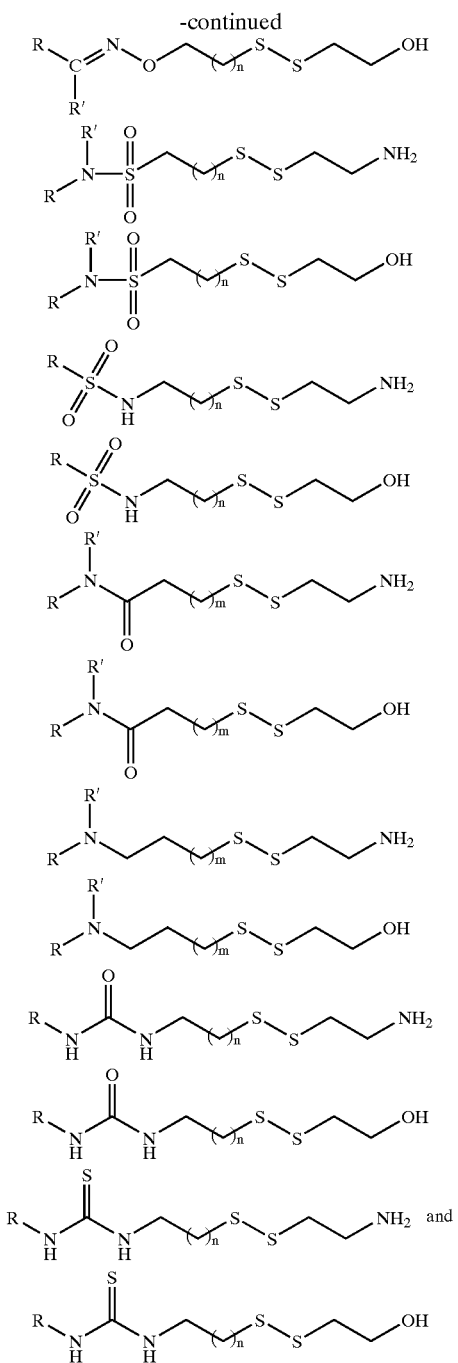

where R and R' are each independently unsubstituted $C_1$–$C_{20}$ aliphatic, substituted $C_1$–$C_{20}$ aliphatic, unsubstituted aryl, or substituted aryl; m is 0, 1, or 2; and n is 1 or 2.

A plurality of ligand candidates comprise a library of ligand candidates. In one embodiment, the library comprises at least 5 ligand candidates. In another embodiment, the library comprises at least 20 ligand candidates. In another embodiment, the library comprises at least 100 ligand candidates. In another embodiment, the library comprises at least 500 ligand candidates. In another embodiment, the library comprises at least 1000 ligand candidates. In another embodiment, each member of the library has a different molecular weight. In another embodiment, each member of the library has a mass that differs from another member of the library by at least 5 atomic mass units. In another embodiment, each member of the library has a mass that differs from another member of the library by at least 10 atomic mass units.

The tethering method wherein the target is a protein and the covalent bond is a disulfide is schematically illustrated in FIG. 1. FIG. 1A illustrates one embodiment of the tethering method where a thiol containing protein is reacted with a plurality of ligand candidates (e.g. >5, >20, >100, >500, >1000, etc.). In this embodiment, the ligand candidates possess a masked thiol in the form of a disulfide of the formula —$SSR^1$ where $R^1$ is as previously defined. In certain embodiments, $R^1$ is selected to enhance the solubility of the potential ligand candidates. As shown, a ligand candidate that possesses an inherent binding affinity for the target is identified and a corresponding ligand that does not include the disulfide moiety is made comprising the identified binding determinant (represented by the circle).

FIG. 1B schematically illustrates the theory behind tethering. A thiol-containing protein is equilibrated with at least one disulfide-containing ligand candidate and equilibrium is established between the modified and unmodified protein. In one embodiment, the thiol-containing protein and the ligand candidate are contacted in the presence of a reducing agent. In another embodiment, the thiol-containing protein and the ligand candidate are contacted in the presence of a substoichometric amount of reducing agent. If the ligand candidate does not have an inherent binding affinity for the target protein, the equilibrium is shifted toward the unmodified protein. In contrast, if the ligand candidate does have an inherent affinity for the protein, the equilibrium shifts toward the modified protein. Both situations are illustrated in FIG. 1B. In the first, the $R^A$ moiety of the ligand candidate possesses little or no binding affinity for the protein. Thus, the formation of the protein-ligand conjugate is a function of the probability of forming a disulfide bond given the concentration of the protein, the ligand candidate, and reducing agent. In the second, the $R^B$ moiety of the ligand candidate possesses an inherent binding affinity for the protein. Consequently, once the disulfide bond is formed between the protein and the ligand candidate, the protein-ligand conjugate is stabilized. Thus, the equilibrium is shifted toward the formation of the protein-ligand conjugate.

To further illustrate tethering, the method has been applied to thymidylate synthase ("TS"), an essential enzyme for virtually all living organisms. TS, along with dihydrofolate reductase ("DHFR") and serine hydroxymethylase, forms a biochemical functional unit, the thymidylate synthase cycle, that provides the sole de novo pathway for synthesis of the DNA base thymidine 5'-monophosphate ("dTMP") from the RNA base dUMP. Both TS and DHRF are targets for anticancer drug development. Because the TS gene is also found in many viruses, it is also a target for development of anti-parasitic, anti-fungal, and anti-viral agents.

TS is an ideal validating target for several reasons. First, numerous high resolution crystal structures of various TS enzymes have been determined so that structural information can be incorporated into compound design. Second, a simple colorimetric assay exists for determining whether a potential ligand binds to TS. This assay depends on the rate of conversion of 5,10-$CH_2$—$H_4$folate to $H_2$folate in the presence of dUMP. A second assay for binding is also spectrophotometric and relies on competition with pyridoxal-5'-phosphate ("PLP"), which forms a complex with TS with a unique spectral signature.

The TS chosen for the purposes of illustration is the *E. coli* TS. Like all TS enzymes, it contains a naturally occurring cysteine residue in the active site (Cys 146) that can be used for tethering. The *E. coli* TS includes four other cysteines but these are not conserved among other TS enzymes and are buried and thus not accessible. However, if one or more of these cysteines were reactive toward disulfides, then mutant versions of these enzymes can be used where these cysteines are mutated to another amino acid such as alanine.

In the first experiment, wildtype TS and the C146S mutant (wherein the cysteine at position 146 has been mutated to serine) were contacted with cystamine, $H_2NCH_2CH_2SSCH_2CH_2NH_2$. The wildtype TS enzyme reacted cleanly with one equivalent of cystamine while the mutant TS did not react indicating that the cystamine was reacting with and was selective for Cys-146.

Figure 2:
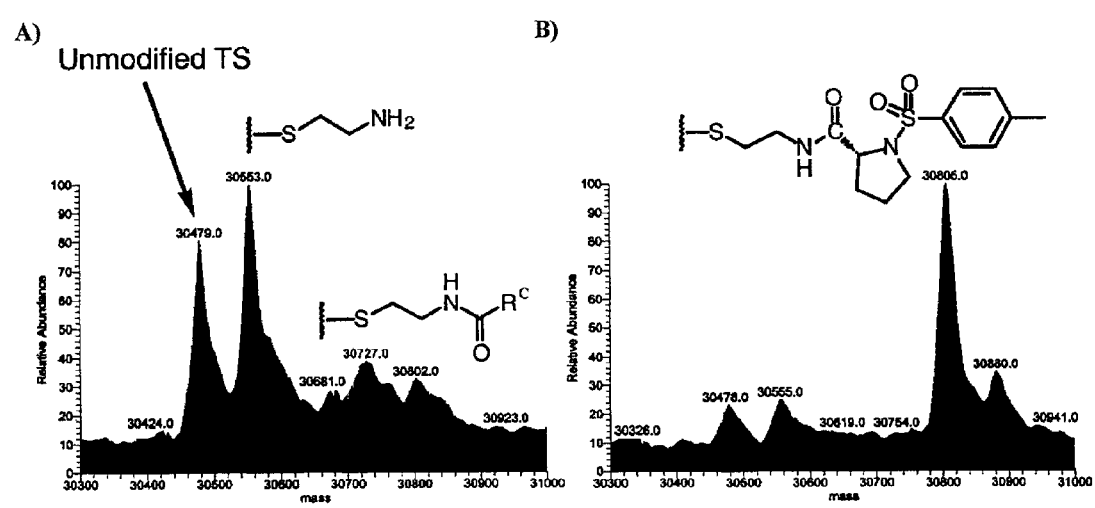
FIG. 2 is a representative example of a tethering experiment.

The wildtype TS was subjected to several tethering experiments with different pools of ligand candidates. FIG. 2 illustrates two representative tethering experiments wherein the ligand candidates were of the formula

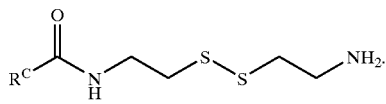

This is a specific embodiment of the genus of ligand candidates of the formula $RSSR^1$ where R corresponds to $R^cC(=O)NHCH_2CH_2—$ and $R^1$ corresponds to $—CH_2CH_2NH_2$. This is also a specific embodiment of the genus of ligand candidates of the formula $RSSR^2R^3$ where R corresponds to $R^cC(=O)NHCH_2CH_2—$ and $R^2R^3$ together correspond to $—CH_2CH_2NH_2$. $R^c$ is unsubstituted $C_1–C_{10}$ alkyl, substituted $C_1–C_{10}$ alkyl, unsubstituted aryl, or substituted aryl, and is the variable moiety among this pool of library members.

FIG. 2A is the deconvoluted mass spectrum of the reaction of TS with a pool of 10 different ligand candidates with little or no binding affinity for TS. In the absence of any binding interactions, the equilibrium in the disulfide exchange reaction between TS and an individual ligand candidate is to the unmodified enzyme. This is schematically illustrated by the following equation.

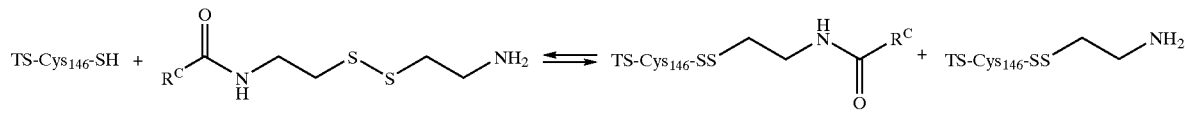

As expected, the peak that corresponds to the unmodified enzyme is one of two most prominent peaks in the spectrum. The other prominent peak is TS where the thiol of Cys146 has been modified with cysteamine. Although this species is not formed to a significant extent for any individual library member, the peak is due to the cumulative effect of the equilibrium reactions for each member of the library pool. When the reaction is run in the presence of a thiol-containing reducing agent such as 2-mercaptoethanol, the active site cysteine can also be modified with the reducing agent. Because cysteamine and 2-mercaptoethanol have similar molecular weights, their respective disulfide bonded TS enzymes are not distinguishable under the conditions used in this experiment. The small peaks on the right correspond to discreet library members. Notably, none of these peaks are very prominent. FIG. 2A is characteristic of a spectrum where none of the ligand candidates possesses an inherent binding affinity for the target.

FIG. 2B is the deconvoluted mass spectrum of the reaction of TS with a pool of 10 different ligand candidates where one of the ligand candidates possesses an inherent binding affinity to the enzyme. As can be seen, the most prominent peak is the one that corresponds to TS where the thiol of Cys146 has been modified with the N-tosyl-D-proline compound. This peak dwarfs all others including those corresponding to the unmodified enzyme and TS where the thiol of Cys146 has been modified with cysteamine. FIG. 2B is an example of a mass spectrum where tethering has captured a moiety that possesses a strong inherent binding affinity for the desired site.

Figure 3:
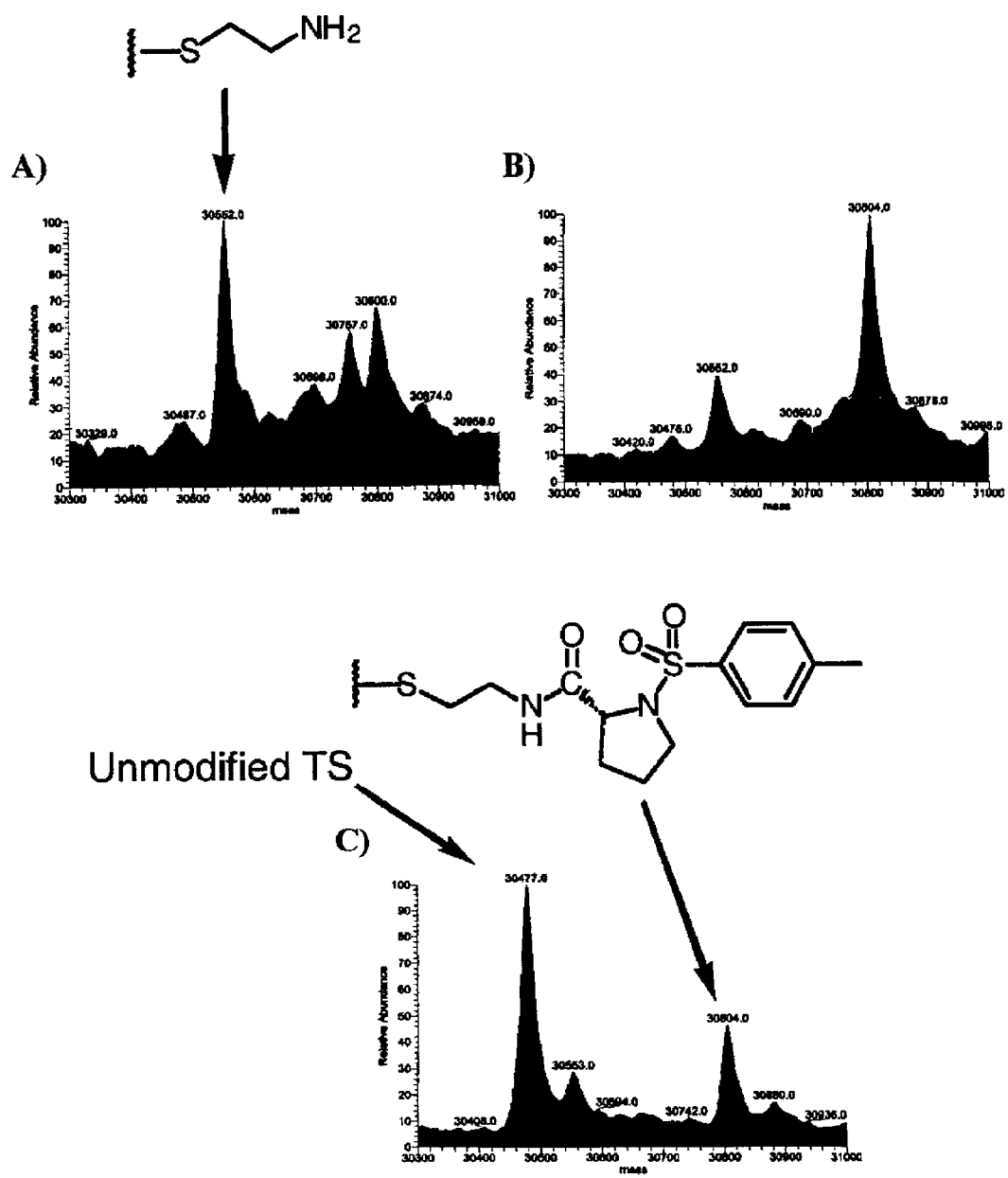
FIG. 3 illustrates the effect of the concentration of reducing agent on an illustrative tethering experiment.

When tethering occurs in the presence of a reducing agent, the process becomes more thermodynamically driven and equilibrium-controlled. FIG. 3 is an illustration of this phenomenon and shows three experiments where TS is reacted with the same library pool containing the selected N-tosyl-D-proline compound in the presence of increasing concentration of the reducing agent, 2-mercaptoethanol.

FIG. 3A is the deconvoluted mass spectrum when the reaction is performed without 2-mercaptoethanol. The most prominent peak corresponds to TS that has been modified with cysteamine. However, the peak corresponding to N-tosyl-D-proline is nevertheless moderately selected over the other ligand candidates. FIG. 3B is the deconvoluted mass spectrum when the reaction is in the presence of 0.2 mM 2-mercaptoethanol. In contrast, to the spectrum in FIG. 3A, the peak corresponding to N-tosyl-D-proline is the most prominent peak and thus is strongly selected over the other ligand candidates. Finally, FIG. 3C is the deconvoluted mass spectrum when the reaction is in the presence of 20 mM 2-mercaptoethanol. Not surprisingly, the most prominent peak under such strongly reducing conditions is the unmodified enzyme. Nevertheless, the peak corresponding to N-tosyl-D-proline is still selected over that of the other ligand candidates in the library pool.

FIG. 3 highlights the fact that the degree of cysteine modification in a target protein by a particular ligand candidate that possesses an inherent affinity for the target is, in part, a function of the reducing agent concentration. In general, the higher the binding affinity of the ligand candidate for the target protein, the higher the concentration of reducing agent that can be used and still get strong selection.

As a result, the concentration of the reducing agent used in the tethering screen can be used as a surrogate for binding affinity as well as to set a lower limit of binding affinity the ligand candidate must have to be strongly selected.

In aspect, the method comprises:
a) contacting a target protein that is capable of forming a disulfide bond with a ligand candidate that is also capable of forming a disulfide bond;
b) forming a disulfide bond between the target protein and the ligand candidate thereby forming a target protein-ligand conjugate;
c) contacting the target protein-ligand conjugate with a reducing agent; and,
d) determining the concentration of reducing agent to decrease the amount of the target protein-ligand conjugate to a desired amount.

The concentration of reducing agent that is required to lower the amounts of the target protein-ligand conjugate is then used as a surrogate for the binding affinity of the ligand candidate of the target protein.

Alternatively, the method can be used to calibrate tethering experiments. An illustrative example of such a calibration is as follows. A first tethering experiment is performed against a plurality of ligand candidates where a strongly selected ligand candidate is identified. Alternatively, a known substrate that has a particular affinity is modified by the addition of a disulfide for example. The identified ligand candidate (or calibration compound) is then used to calibrate the experimental conditions that are required to select only those ligand candidates have a certain minimum binding affinity. In one embodiment, the calibration is the concentration of reducing agent and the calibration compound is used in a series of tethering experiments where a range of concentrations of reducing agent is used. An example is where the method comprises:

a) contacting a target protein that is capable of forming a disulfide bond with a calibration compound that is also capable of forming a disulfide bond;
b) forming a disulfide bond between the target protein and the calibration compound thereby forming a target protein-calibration compound conjugate;
c) contacting the target protein-calibration compound conjugate with a reducing agent; and,
d) determining the concentration of reducing agent required to decrease the amount of the target protein-calibration compound conjugate to a desired amount.

In general, lower concentrations of reducing agent will result in a higher percentage of the target being modified with the calibration compound and vice versa. In one embodiment, the desired amount is 50%. In other words, about 50% of the target protein is in the unmodified form and the remaining about 50% is as the target protein-calibration compound conjugate. Thus, the concentration of reducing agent that is associated with the desired amount (which in this case is about 50%) is used in subsequent tethering experiments to require that a ligand candidate have some lower level of binding affinity to be selected. Illustrative examples of other desired amounts that can be used depending on the desired lower level of binding affinity include about 20%, 25%, 30%, 40% 60% 75% and the like.

Figure 4:
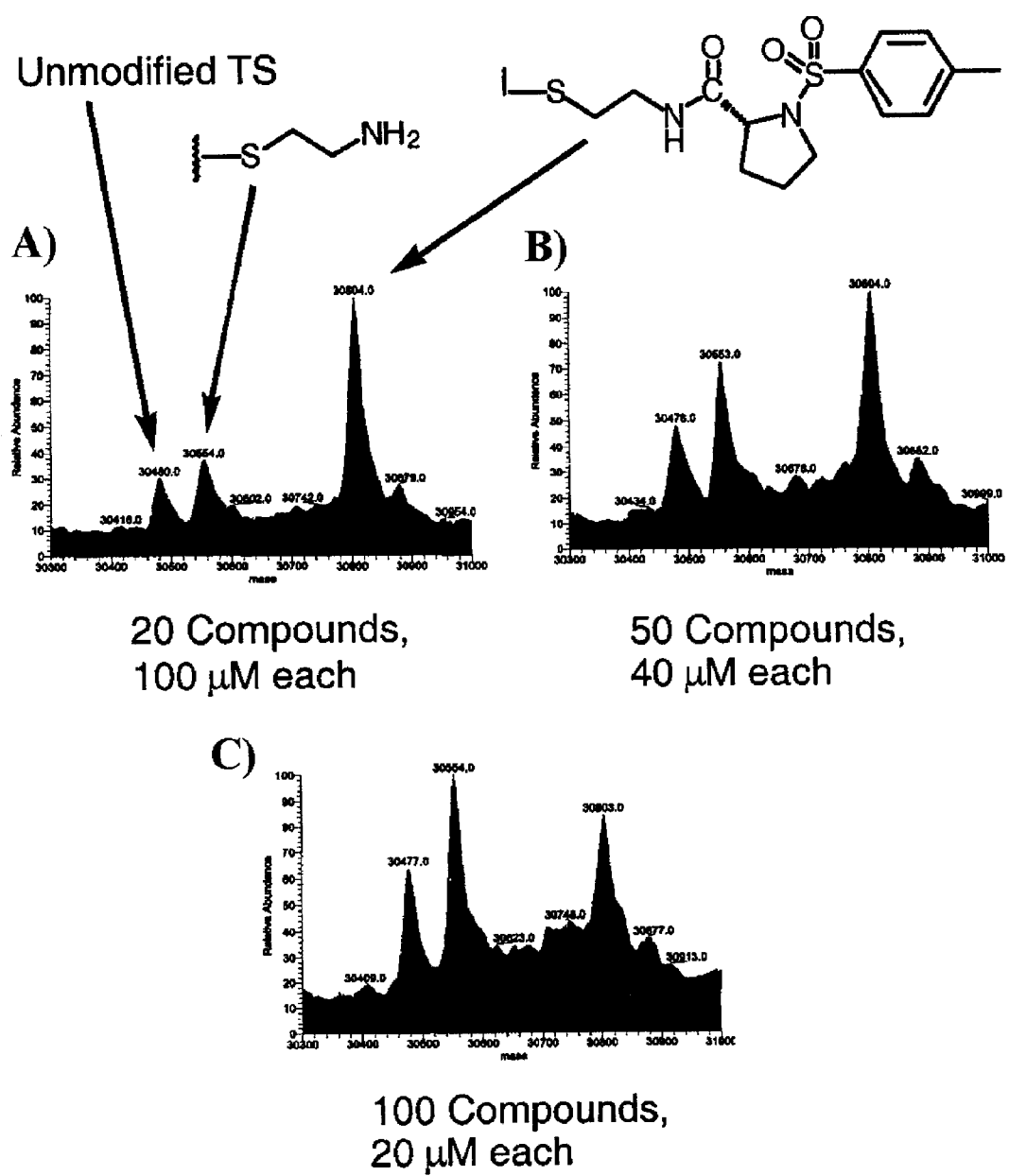
FIG. 4 illustrates the effect of the number of ligand candidates in a library in a typical tethering experiment.

As stated previously, the tethering method can be used with a single ligand candidate or a plurality of ligand candidates. In preferred embodiments, the tethering method is used to screen a plurality of ligand candidates (e.g., 5, 20, 100, 500, 1000, and even >1000) to maximize throughput and efficiency. FIG. 4 shows the results of an experiment where the number of ligand candidates in a library pool was varied. Although this experiment shows that N-tosyl-D-proline is strongly selected even when the pool contains 100 ligand candidates, libraries containing even larger numbers of ligand candidates (e.g., >500, >750, >1000) are now routinely used.

A structure-activity relationship ("SAR") can be developed using information from a tethering experiment in much the same way SAR is developed using traditional assays. For example, ligand candidates with $R^c$s on the left hand side of the scheme below were strongly selected against the E. coli TS but those ligand candidates with $R^c$s on the right hand side were not.

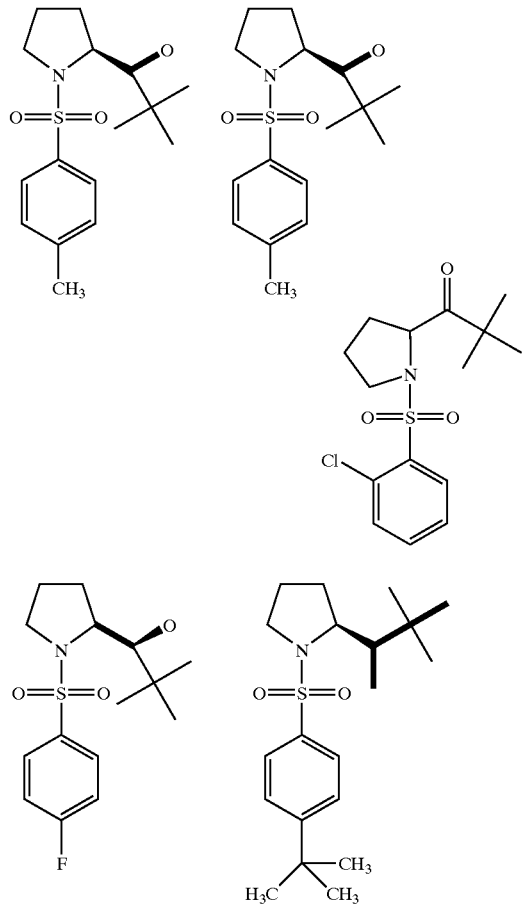
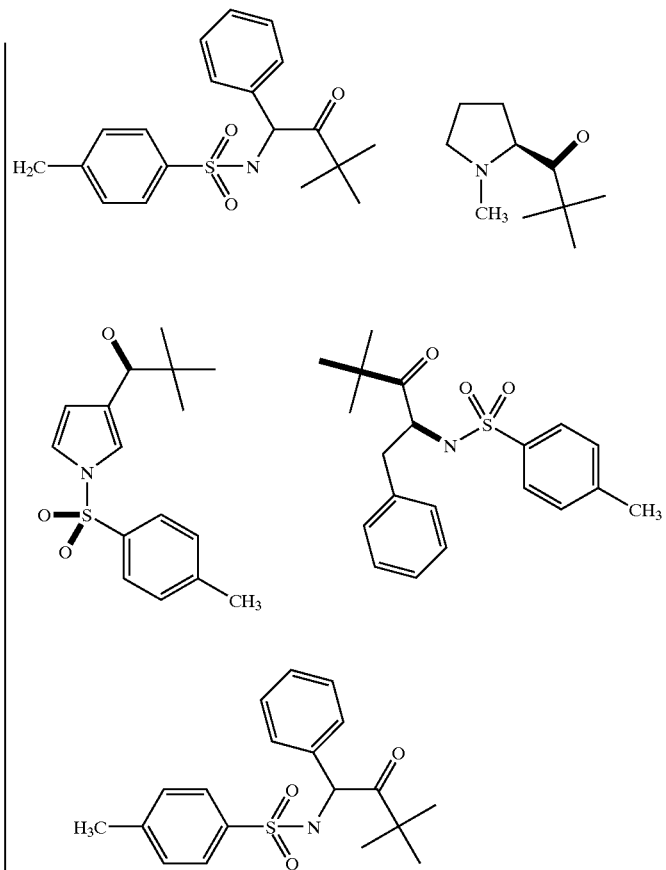

Based on the data from screening approximately 1200 compounds, it was determined that the phenyl-sulfonamide core and the proline ring are essential. For example, although TS appears to accommodate a great deal of flexibility around the phenyl ring where the phenyl ring can be unsubstituted or substituted with a range of groups including methyl, t-butyl, and halogen, its presence is required for selection. Similarly, the proline ring appears essential because compounds where it was replaced with phenylalanine, phenylglycine or pyrrole were not selected.

In addition to the above, further experiments were performed to validate that the compounds selected from tethering correspond to those with binding affinity for the target. In one illustrative example, the tethering experiment is performed in the presence of a known substrate. If the selected ligand candidate possesses an inherent binding affinity for the target, it would be resistant to displacement by the substrate. In contrast, a ligand candidate that lacks an inherent binding affinity or cysteamine would be easily displaced by the substrate. Another illustrative example is traditional enzymatic assays on the tether-free analog. For example, the affinity of the

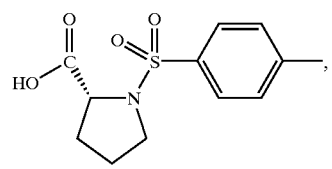

1

$R^c$ portion of the ligand fragment was determined using Michaelis-Mention kinetics. The $K_i$ of the free acid 1 was 1.1±0.25 mM. Notably, the free acid competed with the natural substrate dUMP. Thus, N-tosyl-D-proline 1 is a weak but competitive inhibitor of TS In another embodiment, the naturally occurring cysteine residue in the active site was mutated to a serine (C146S) and another cysteine was introduced (L143C or H147C). Tethering using the C146S/L143C mutant produced similar results as the wild type enzyme. Notably, the N-tosyl-D-proline analog was strongly selected. In contrast, the C146S/H147C did not select the N-tosyl-D-proline analog but several other molecules were selected. These results are believed to reflect the differences in the local binding environment surrounding the reactive cysteine and the geometric constraints of the disulfide linker.

X-ray crystallography was used to solve the three-dimensional structures of the native enzyme and several complexes to confirm that the information obtained from tethering can be correlated with productive binding to the target. Table 1 details crystallographic data and refinement parameters. One complex was of the free acid of N-tosyl-D-proline bound to TS (fourth entry in Table 1). Another complex was of the N-tosyl-D-proline derivative tethered to the active site cysteine (Cys-146) (second entry in Table 1). Yet another complex was of N-tosyl-D-proine derivative tethered to the C146S/L143C mutant (third entry in Table 1).

TABLE 1

| Data set | Space group* | Cell dimensions, Å | Resolution, Å | Reflections (no.) Overall | Reflections (no.) Unique | Completeness,† % | $R_{sym}$ (I),‡% | I/σ | $R_{cryst}$,§ % | $R_{free}$,π % | rms deviation bond lengths, Å | rms deviation bond angles, deg |
|---|---|---|---|---|---|---|---|---|---|---|---|---|
| Native C146 | I2₁3 | a = 131.17 | 10–1.75 | 104,019 | 36,586 | 96.7 (91.6) | 4.9 (33.8) | 20.5 (4.0) | 19.8 | 24.4 | 0.010 | 2.30 |
| tethered N-tosyl-D-proline | P6₃ | a = 126.22 c = 67.02 | 10–2.00 | 97,445 | 41,001 | 98.8 (94.5) | 4.4 (26.0) | 14.7 (4.1) | 19.8 | 26.8 | 0.010 | 2.59 |
| L143C tethered N-tosyl-D-proline | P6₃ | a = 126.33 c = 67.12 | 10–2.15 | 78,793 | 32,045 | 96.7 (92.1) | 8.1 (28.6) | 12.8 (4.5) | 19.6 | 26.7 | 0.014 | 3.06 |
| Noncovalent N-tosyl-D-proline | I2₁3 | a = 131.88 | 10–1.90 | 202,300 | 31,422 | 100 (100) | 7.4 (28.2) | 19.7 (3.8) | 19.2 | 23.8 | 0.011 | 2.49 |
| Glu-TP | P6₃ | a = 126.14 c = 66.81 | 10–2.00 | 143,599 | 40,497 | 99.4 (96.9) | 8.5 (31.9) | 13.9 (4.0) | 19.4 | 25.1 | 0.007 | 2.15 |
| Glu-TP-βAla | P6₃ | a = 126.03 c = 66.84 | 10–1.75 | 142,016 | 58,487 | 95.8 (85.2) | 4.0 (22.5) | 17.1 (4.9) | 18.0 | 21.4 | 0.007 | 2.00 |

This is not a "true" free R factor because the starting model was a fully refined structure. However, the free R factor set of reflections was kept constant for each of the above refinements.
*The I2₁3 crystal contains one monomer per asymmetric unit. The P6₃ form contains the biologically relevant homodimer.
†Values in parentheses are for the highest resolution bin.
‡$R_{sym}$ (f) = $\Sigma_{hkl}|I_{hlk}|\Sigma_{hkl}I_{hkl}$, where $I_{hkl}$ is the intensity of reflection$_{hkl}$.
§$R_{cryst}$ = $\Sigma_{hkl}||F_{obs}| - |F_{calc}||/|F_{obs}|$, where $F_{obs}$ and $F_{calc}$ are the observed and calculated structure factors, respectively, for the data used in refinement.
π$R_{free}$ = $\Sigma_{hkl}||F_{obs}| - |F_{calc}||/|F_{obs}|$, where $F_{obs}$ and $F_{calc}$ are the observed and calculated structure factors, respectively, for 10% of the data omitted from refinement.

Significantly, the location of the N-tosyl-D-proline moiety is very similar in all three cases (RMSD of 0.55–1.88 Å, compared to 0.11–0.56 Å for all Cα carbons in the protein). The fact that the N-tosyl-D-proline substituents closely overlap while the alkyl-disulfide tethers converge onto this moiety from different cysteine residues supports the notion that the N-tosyl-D-proline moiety, not the tether, is the binding determinant.

As can be seen, tethering is a powerful method that can identify ligands that bind to a site of interest in a target. Tethering can be used alone or in combination with other medicinal chemistry methods to identify and optimize a drug candidate.

Figure 5:
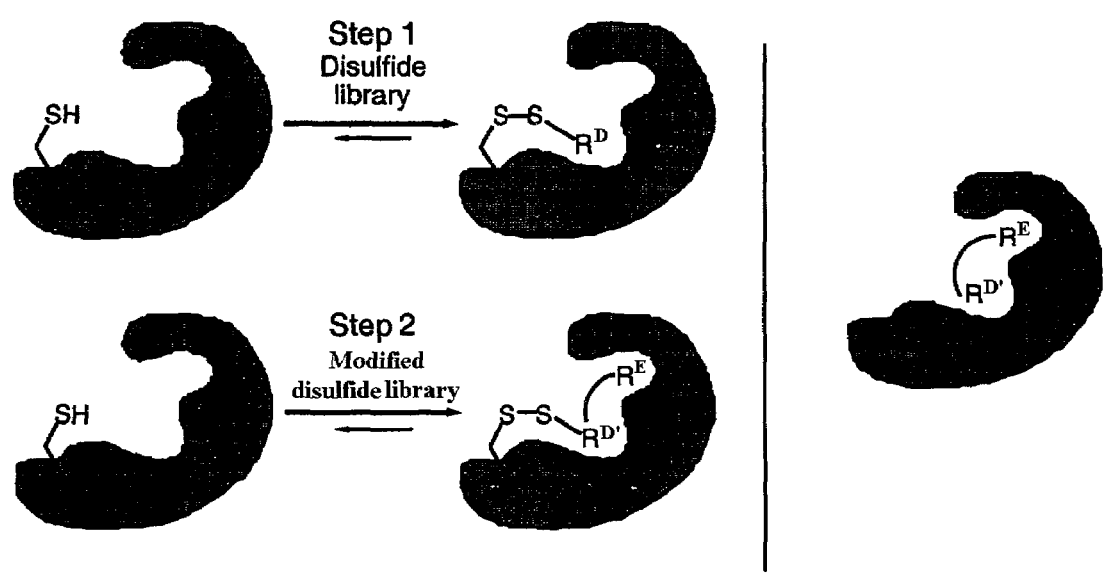
FIG. 5 is a schematic representation where the originally selected binding determinant $R^D$ was used to make a library of compounds that comprise $R^D$ as well as variants thereof. This figure illustrates a tethering experiment where the modified library included a compound that included a variant of the first binding determinant, $R^{D'}$, as well as a second binding determinant $R^E$. As shown, these two binding determinants are subsequently linked together to form a conjugate molecule that lacks the disulfide.

In one aspect of the present invention, tethering is used to identify a binding determinant (e.g. $R^c$) and then traditional medicinal chemistry is used to make higher affinity compounds containing the identified binding determinants or variations thereof. In one embodiment, tethering is used to both identify a binding determinant and also used to assess whether compounds bind to the target with higher affinity. For example, tethering is an alternative to traditional binding experiments where either functional assays are not available or are susceptible to artifacts. This approach is schematically illustrated in FIG. 5. As can be seen, tethering is used to identify a binding determinant $R^D$. Once such a binding determinant is identified, traditional medicinal chemistry approaches are used to synthesize variants of $R^D$ in a modified library. The modified library of ligand candidates would include variants of $R^D$ such as isosteres and homologs thereof. The modified library can also include "extended" compounds that include $R^D$ or variations thereof as well as other binding determinants that can take advantage of adjacent binding regions. FIG. 5 illustrates a selected compound from the modified library wherein the original binding determinant $R^D$ was modified to $R^{D'}$ and the selected compound includes a second binding determinant $R^E$. Example 6 further illustrates this method with respect to the optimization effort of low micromolar affinity compounds (2 and 3) for TS that were identified from the optimization of compound 1, a low millimolar compound.

In another aspect of the present invention, methods are provided for identifying two binding determinants that are subsequently linked together. In general, the method comprises:
a) identifying a first compound that binds to a target protein;
b) identifying a second compound that binds to the target protein; and,
c) linking the first compound and second compound through a linker element to form a conjugate molecule that binds to the target protein. In preferred embodiments, the conjugate molecule binds to the target protein with higher binding affinity than either the first compound or second compound alone.

Figure 6:
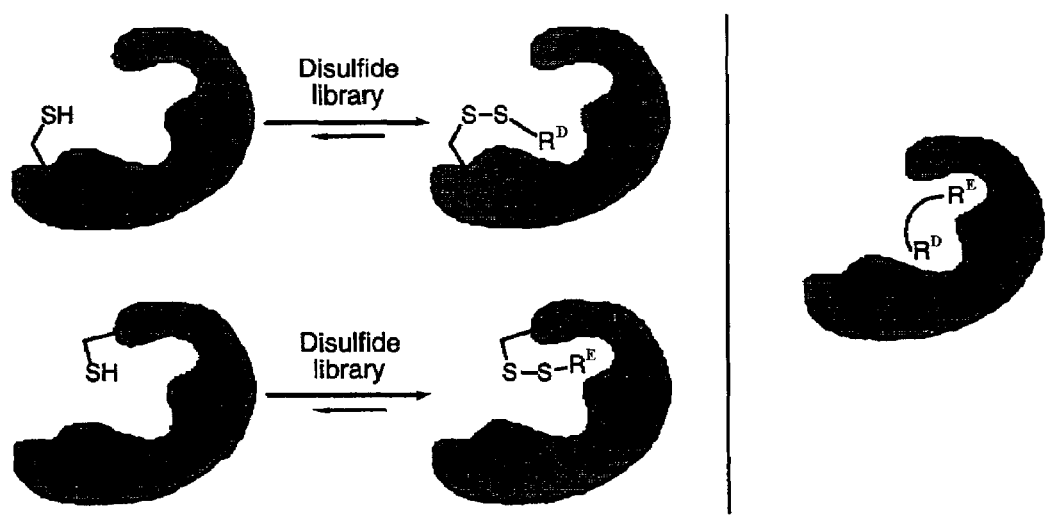
FIG. 6 is a schematic of two tethering experiments that are used to identify two binding determinants, $R^D$ and $R^E$ which are subsequently linked together to form a conjugate molecule.

In one embodiment, the first compound is of the formula $R^D SSR^1$ and the second compound is of the formula $R^E SSR^1$ (where R and $R^1$ are as previously described and $R^D$ and $R^E$ are each independently $C_1$–$C_{20}$ unsubstituted aliphatic, $C_1$–$C_{20}$ substituted aliphatic, unsubstituted aryl, or substituted aryl) and the first and second compounds bind to the target protein through a disulfide bond. FIG. 6 is a schematic illustration of this method where two separate tethering experiments are used to identify binding determinants $R^D$ and $R^E$ that are subsequently linked together to form a conjugate molecule that binds to the target protein.

Figure 7:
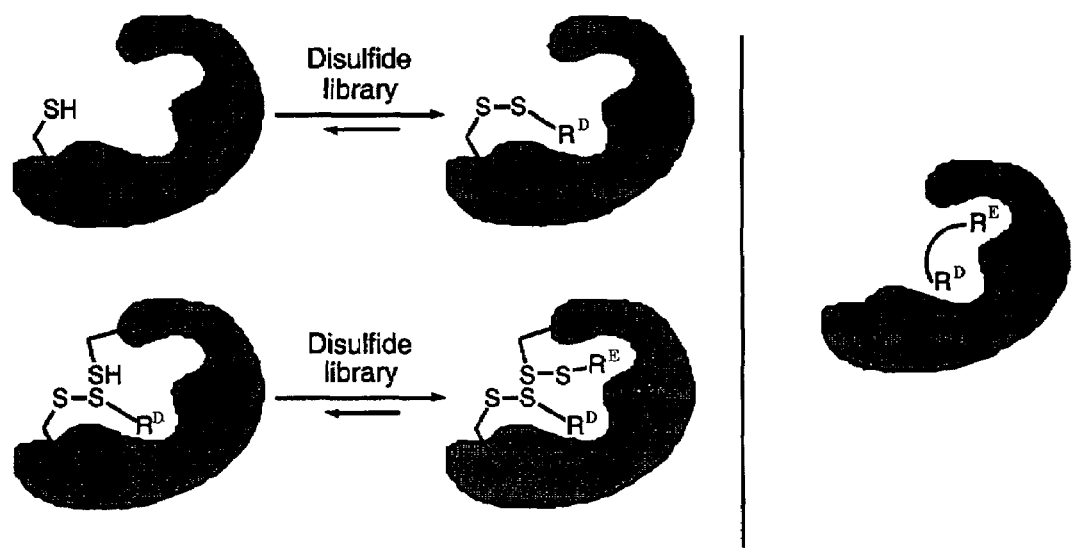
FIG. 7 is a schematic of two tethering experiments where the second binding determinant $R^E$ is identified in the presence of the binding of $R^D$. Once identified, the two binding determinants are then linked to form a conjugate molecule.

In another embodiment, the tethering experiments to identify binding determinants $R^D$ and $R^E$ occur simultaneously. In this way, it is assured that the two identified binding determinants bind to the target protein at non-overlapping sites. Thus, the method comprises:
a) identifying a first compound that binds to a target protein;
b) identifying a second compound that binds to the target protein in the presence of the first compound bound to the target protein; and,
c) linking the first compound and second compound through a linker element to form a conjugate molecule that binds to the target protein. FIG. 7 is a schematic illustration of this method. In the first tethering experiment, the binding determinant $R^D$ is identified. Once $R^D$ is identified, a second reactive cysteine is either introduced or unmasked and a tethering experiment to identify a binding determinant $R^E$ occurs in the presence of the binding determinant $R^D$. The two binding determinants, $R^D$ and $R^E$ are subsequently linked to form a conjugate molecule that binds to the target protein In another embodiment, the first compound is identified using tethering and the second compound is identified through a non-tethering method. In one embodiment, the non-tethering method comprised rational drug design and traditional medicinal chemistry. The crystal structure of N-tosyl-D-proline bound to TS revealed that the tosyl group is in roughly the same position and orientation as the benzamide moiety of methylenetetrahydrofolate, the natural cofactor for the TS enzyme. Consequently, the glutamate moiety of methylenetetrahydrofoloate was grafted onto compound 1. Table 2 shows a selected number of these compounds.

TABLE 2

| COMPOUND | WHERE R = | $K_i$ |
|---|---|---|
| 4 (L-proline) | (CO$_2$H, CO$_2$H) | 83 ± 5 μM |
| 5 (D-proline) | (CO$_2$H, CO$_2$H) | 24 ± 7 μM |
| 6 | (CO$_2$H, CO$_2$H) | 242 ± 3 μM |
| 7 | (CO$_2$H, CO$_2$H) | 23 ± 6 μM |

TABLE 2-continued

| COMPOUND | WHERE R = | $K_i$ |
|---|---|---|
| | [structure: pyrrolidine-N-sulfonyl-phenyl-C(O)-NH-R with CO2H on pyrrolidine] | |
| 8 | [structure: CH(CO2H)–(CH2)3–CO2H] | $32 \pm 2$ μM |
| 9 | [structure: CH(CO2H)–(CH2)5–CO2H] | $14 \pm 6$ μM |
| 10 | [structure: CH(CONH2)–(CH2)2–CO2H] | $378 \pm 69$ μM |
| 11 | [structure: CH(CO2H)–(CH2)2–CONH2] | $61 \pm 14$ μM |
| 12 | [structure: –(CH2)3–CO2H] | $246 \pm 46$ μM |

There is a distinct preference for the D-enantiomer of proline (compound 5) over the L-enantiomer (compound 4) and the α-carboxylate of the glutamate residue is important because removing it (compound 12) or changing it to a primary amide (compound 10) correlates with a significant loss in binding affinity.

In another aspect of the present invention, a variation on the tethering method is provided for use in making and optimizing compounds. In general, this method comprises,
a) providing a target having an anchoring group that is capable of forming a covalent bond or coordinating a metal at or near a site of interest;
b) contacting the target with an extender thereby forming a target-extender complex wherein the extender comprises a first functionality that forms either a covalent bond or coordinates a metal and a second functionality that is capable for forming a covalent bond;
c) contacting the target-extender complex with a candidate ligand that comprises a group that is capable of forming a covalent bond with the second functionality;
d) forming a covalent bond between the target-extender complex and the candidate ligand; and
e) identifying the candidate ligand present in the target-extender-ligand conjugate.

In one embodiment, the anchoring group in the target is a reactive nucleophile or an electrophile and forms an irreversible covalent bond with the first functionality of the extender. In another embodiment, the anchoring group in the target is a reactive nucleophile or an electrophile and forms a reversible covalent bond with the first functionality of the extender. In another embodiment, the anchoring group in the target is a metal coordination site and the anchoring group together with the first functionality forms a metal coordination site. Illustrative examples of suitable metals that are capable of binding to such sites include Cd, Hg, As, Zn, Fe, Cu, Ni, Co and Ca. In another embodiment, the second functionality is a reactive nucleophile or a reactive electrophile.

In preferred embodiments, the extender comprises a first and second functionalities as described above and includes a binding determinant that possesses an inherent binding affinity for the target. If the binding determinant does not already include a first and second functionality, then it can be modified to contain them. In one method, tethering is used to identify a binding determinant $R^c$ that is then modified to include a first and second functionalities. In another method, the binding determinant is obtained from known substrates of the target or fragments thereof.

In another embodiment, the anchoring group in the target is a reactive nucleophile and the extender comprises a first functionality that is capable of forming a covalent bond with a nucleophile and a second functionality that is capable of forming a disulfide bond. The method comprises:
a) providing a target having a reactive nucleophile at or near a site of interest; and
b) contacting the target with an extender thereby forming a target-extender complex wherein the extender comprises a first functionality that reacts with the nucleophile in the target to form a covalent bond and a second functionality that is capable of forming a disulfide bond;
c) contacting the target-extender complex with a ligand candidate that is capable of forming a disulfide bond;
d) forming a disulfide bond between the target-extender complex and the ligand candidate thereby forming a target-extender-ligand conjugate; and
e) identifying the ligand candidate present in the target-extender-ligand conjugate. Optionally, the target is contacted with a ligand candidate in the presence of a reducing agent.

Illustrative examples of suitable reducing agents include but are not limited to: cysteine, cysteamine, dithiothreitol, dithioerythritol, glutathione, 2-mercaptoethanol, 3-mercaptoproprionic acid, a phosphine such as tris-(2-carboxyethylphosphine) ("TCEP"), or sodium borohydride. In one embodiment, the reducing agent is 2-mercaptoethanol. In another embodiment, the reducing agent is cysteamine. In another embodiment, the reducing agent is glutathione. In another embodiment, the reducing agent is cysteine.

In one embodiment, the target comprises a —OH as the reactive nucleophile and the extender comprises a first functionality that is capable of forming a covalent bond with the reactive nucleophile on the target and a second functionality that is capable of forming a disulfide bond. In another embodiment, the reactive nucleophile on the target is a —OH from a serine, threonine, or tyrosine that is part of the naturally occurring protein sequence. In another embodiment, the reactive nucleophile on the target is an engineered —OH group where mutagenesis was used to mutate a naturally occurring amino acid to a serine, threonine, or tyrosine. In another embodiment, the first functionality of the extender is a boronic acid and the second functionality is a —SH or a masked —SH. An illustrative example of a masked —SH is a disulfide of the formula —SSR$^1$ where $R^1$ is as previously described.

In another embodiment, the target comprises a —SH as the reactive nucleophile and the extender comprises a first functionality that is capable of forming a covalent bond with the reactive nucleophile on the target and a second functionality that is capable of forming a disulfide bond. In one embodiment, the reactive nucleophile on the target is a naturally occurring —SH from a cysteine that is part of the naturally occurring protein sequence. In another embodiment, the reactive nucleophile on the target is an engineered —SH group where mutagenesis was used to mutate a naturally occurring amino acid to a cysteine.

In another embodiment, the target protein possesses a masked —SH in the form of a disulfide as the reactive nucleophile. In another embodiment, the target protein possesses a cysteine where the thiol is masked as a disulfide. In another embodiment, the target protein possesses a cysteine where the thiol is masked as a disulfide bond with another cysteine. In another embodiment, the target protein possesses a cysteine where the thiol is masked as a disulfide bond with glutathione. In another embodiment, the target protein possesses a cysteine where the thiol is masked as a disulfide of the formula —SSR$^1$ where R$^1$ is as previously described.

In one embodiment, the first and second functionalities of the extender are each independently a —SH or a masked —SH. An illustrative example of a masked thiol is a disulfide of the formula —SSR$^1$ where R$^1$ is as previously described. In this embodiment, the covalent bond formed between the target and the extender is a disulfide bond and thus is a reversible covalent bond. In one variation of the method, the target is contacted with the extender prior to contacting the target-extender complex with one or more ligand candidates. In another variation, the target is contacted with a pool comprising the extender and one or more ligand candidates.

In another embodiment, the first functionality is a group that is capable of forming an irreversible covalent bond with the reactive nucleophile of the target under conditions that do not denature the target and the second functionality is a —SH or a masked —SH. In one embodiment, the first functionality is a group capable of undergoing SN2—like addition. Illustrative example of such extenders include: (i) α-halo acids such as

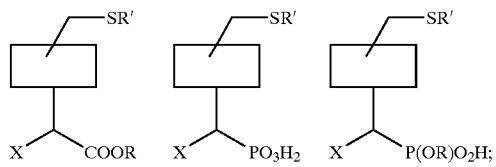

(ii) fluorophosphonates such as

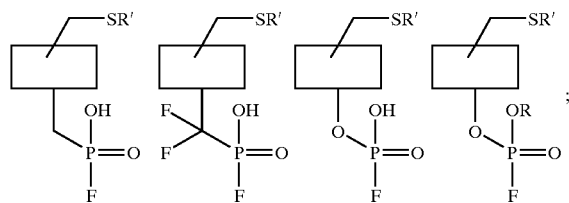

(iii) epoxides such as

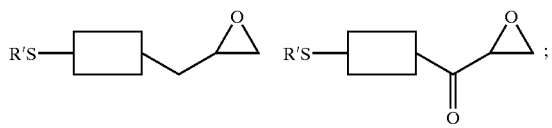

(iv) aziridines such as

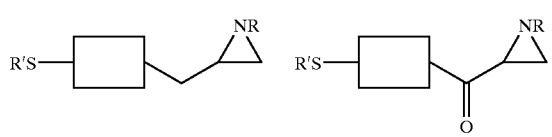

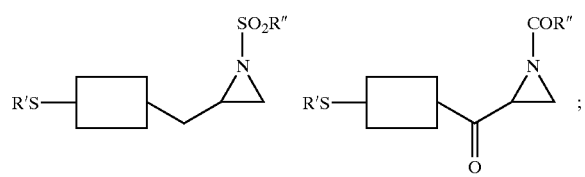

(v) thiiranes such as

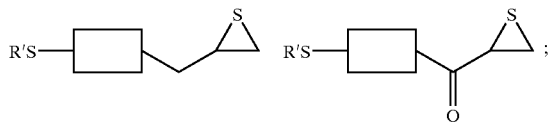

(vi) halomethyl ketones/amides such as

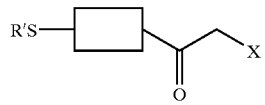

where R is unsubstituted $C_1$–$C_{20}$ aliphatic, substituted $C_1$–$C_{20}$ aliphatic, unsubstituted aryl, and substituted aryl; R' is H, —SR$^1$ wherein R$^1$ has been previously defined; and X is a leaving group. Illustrative examples of include halogen, $N_2$, OR, —P(=O)Ar2, —NO(C=O)R, —(C=O)R, —SR and vinyl sulfones. In these and other structures illustrated below, the boxes represent binding determinants within the small molecule extenders (SME's), i.e. represent the part of the SME that has binding affinity for the target.

In another embodiment, the first functionality is a group capable of undergoing SN aryl like addition. Illustrative examples of suitable groups include 7-halo-2,1,3-benzoxadiazaoles, and ortho/para nitro substituted halobenzenes such as

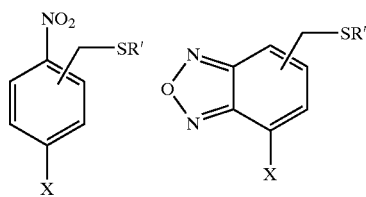

where R' and X are as previously defined.

In another embodiment, the first functionality is a group capable of undergoing Michael-type addition. Illustrative examples of suitable groups include any moiety that includes a double or triple bond adjacent to an electron withdrawing system such as a carbonyl, imines, quinines, CN, $NO_2$, and —S(=O)—. Illustrative examples of such extenders include:

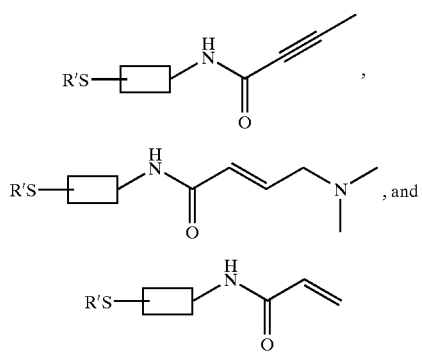

where R' is as previously defined.

Extenders are often customized for a particular target or a family of targets. An illustrative example of kinase specific extenders include:

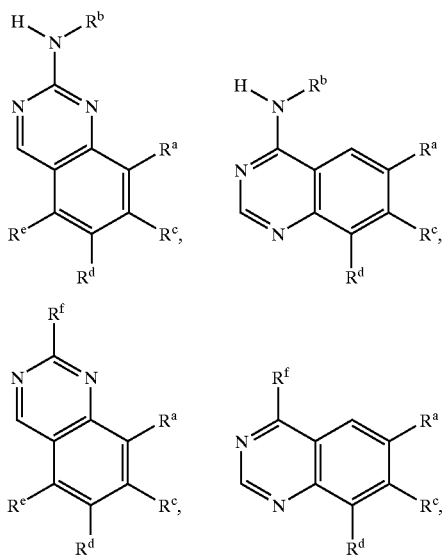

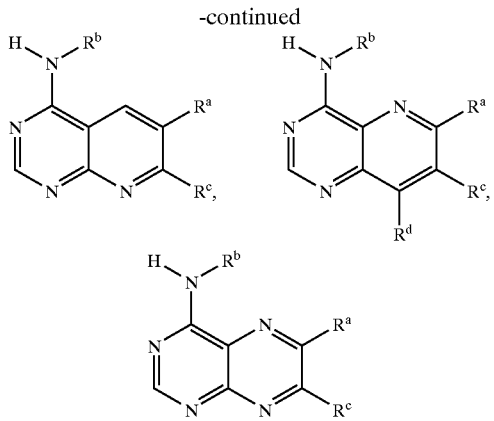

where $R^a$, $R^b$, $R^c$, $R^d$, $R^e$, and $R^f$ are each independently selected from the group consisting of hydrogen, $C_1$–$C_5$ alkyl, $C_1$–$C_5$ alkylamine, and aryl provided that at least one R group on the extender is a Michael acceptor and another R group is selected from —$(CH_2)_n$—SR'; —C(=O)—$(CH_2)_n$—SR'; —O—$(CH_2)_n$—SR'; —$(CH_2)_n$—SR'; and a thiol protecting group wherein R' is as previously described. Illustrative examples of suitable Michael acceptors include

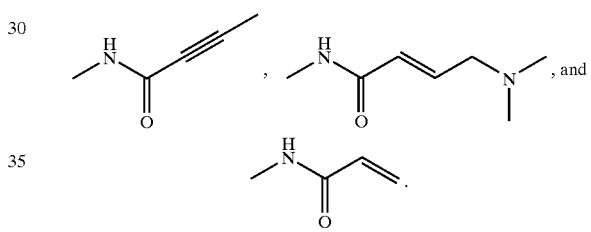

An illustrative example of serine protease specific extenders include:

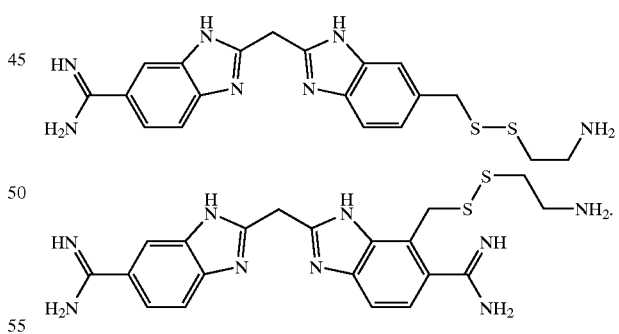

The first functionality in these extenders is a metal coordination site and the second functionality is a masked thiol in the form of —$SSCH_2CH_2NH_2$ although it could in the form of —$SSR^1$ where $R^1$ is as previously described. These extenders bind to a serine protease only in the presence of zinc (see Katz et al., *Nature* 391: 608–12 (1998); Katz and Luong, *J. Mol. Biol.* 292: 669–84 (1999); Janc et al., *Biochemistry* 39: 4792–800 (2000). A version of this compound that lack the second functionality bind to the active site of a serine protease through the active site histidine and serine as shown below

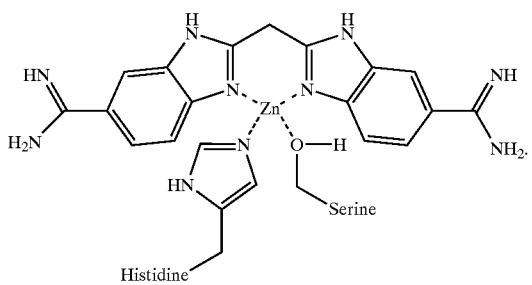

Figure 8:
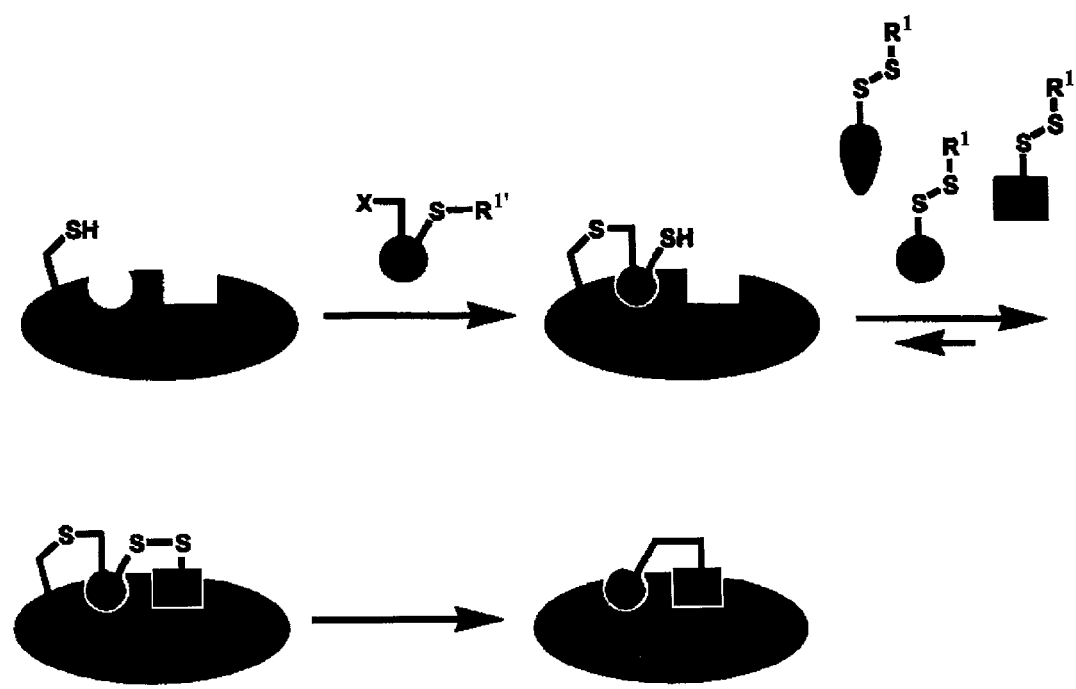
FIG. 8 is a schematic representation of one embodiment of a tethering method where an extender comprising a first and second functionality is used. As shown, a target that includes a thiol is contacted with an extender comprising a first functionality X that is capable of forming a covalent bond with the reactive thiol and a second functionality second functionality —$SR^{1'}$ that is capable of forming a disulfide bond. A tether-extender complex is formed which is then contacted with a plurality of ligand candidates. The extender provides one binding determinant (circle) and the ligand candidate provides the second binding determinant (square) and the resulting binding determinants are linked together to form a conjugate compound.

FIG. 8 illustrates one embodiment of the tethering method using extenders. As shown, a target that includes a reactive nucleophile —SH is contacted with an extender comprising a first functionality X that is capable of forming a covalent bond with the reactive nucleophile and a second functionality —SR$^{1'}$ (where R$^{1'}$ is the same as R$^1$ as defined above) that is capable of forming a disulfide bond. A tether-extender complex is formed which is then contacted with a plurality of ligand candidates. The extender provides one binding determinant (circle) and the ligand candidate provides the second binding determinant (square) and the resulting binding determinants are linked together to form a conjugate compound.

Synthetic methods for forming a reversible or irreversible covalent bond between reactive groups on a target and a ligand, a target and an extender, a target-extender complex and a ligand, or between two ligands, are well known in the art, and are described in basic textbooks, such as, e.g. March, *Advanced Organic Chemistry*, John Wiley & Sons, New York, 4$^{th}$ edition, 1992. Reductive aminations between aldehydes and ketones and amines are described, for example, in March et al., supra, at pp. 898–900; alternative methods for preparing amines at page 1276; reactions between aldehydes and ketones and hydrazide derivatives to give hydrazones and hydrazone derivatives such as semicarbazones at pp. 904–906; amide bond formation at p. 1275; formation of ureas at p. 1299; formation of thiocarbamates at p. 892; formation of carbamates at p. 1280; formation of sulfonamides at p. 1296; formation of thioethers at p. 1297; formation of disulfides at p. 1284; formation of ethers at p. 1285; formation of esters at p. 1281; additions to epoxides at p. 368; additions to aziridines at p. 368; formation of acetals and ketals at p. 1269; formation of carbonates at p. 392; formation of denamines at p. 1264; metathesis of alkenes at pp. 1146–1148 (see also Grubbs et al.,*Acc. Chem. Res.* 28:446–453 [1995]); transition metal-catalyzed couplings of aryl halides and sulfonates with alkanes and acetylenes, e.g. Heck reactions, at p.p. 717–178; the reaction of aryl halides and sulfonates with organometallic reagents, such as organoboron, reagents, at p. 662 (see also Miyaura et al., *Chem. Rev.* 95:2457 [1995]); organotin, and organozinc reagents, formation of oxazolidines (Ede et al., *Tetrahedron Letts.* 28:7119–7122 [1997]); formation of thiazolidines (Patek et al., *Tetrahedron Letts.* 36:2227–2230 [1995]); amines linked through amidine groups by coupling amines through imidoesters (Davies et al., *Canadian J. Biochem. c*50:416–422 [1972]), and the like.

To further illustrate the tethering method using extenders, the method has been applied to a anti-apoptotic target caspase-3, a member of the cysteine aspartyl protease family. There are currently about a dozen known members of the caspase family, many of which are involved in the initiation or propagation of the apoptotic cascade. Caspases are potential drug targets for a variety of therapeutic indications involving excessive or abnormal levels of programmed cell death such as stroke, traumatic brain injury, spinal cord injury, Alzheimer's disease, Huntington's disease, Parkinson's disease, cardiovascular diseases, liver failure, and sepsis. Moreover, caspase-3 includes a naturally occurring cysteine residue at the active site and has been well characterized both functionally and crystallographically.

A suitable extender for use in the caspase-3 active site was designed using the fact that small aspartyl-based arylacyloxymethyl ketones are known to react irreversibly with the active site cysteine. Examples 7–10 and 14 describe the syntheses of five illustrative extenders. These extenders can also be used in tethering experiments with other caspase targets such as caspase-1 and caspase-7. Two extenders that will be described in greater detail are compounds 13 and 14.

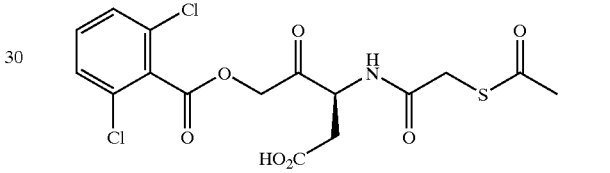

13

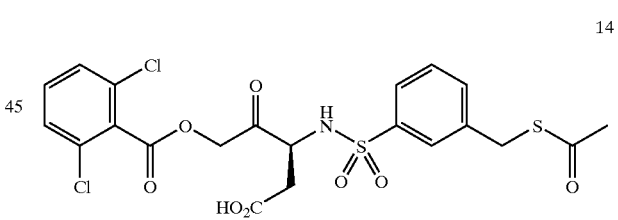

14

As can be seen, compounds 13 and 14 include an aspartic acid moiety as the binding determinant. Notably, the carbonyl of the aspartic acid moiety is also part of the first functionality (the arylacyloxymethyl ketone moiety) that forms a covalent bond with the thiol of the active site cysteine. Extenders 13 and 14 also include a second functionality, a masked —SH in the form of a thioester that can be unmasked at the appropriate time. For example, the thioester can be converted into the free thiol by treating the target-extender complex with hydroxylamine.

Both extenders were shown to selectively modified caspase-3 at the active site cysteine and were treated with hydroxylamine to generate the following target-extender complexes:

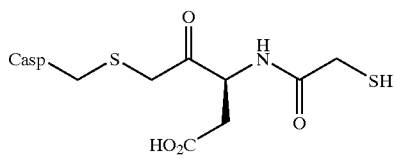

13'

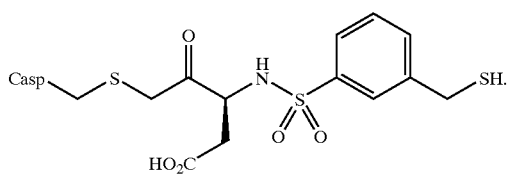

14'

Example 11 describes the procedure in greater detail with respect to the modification of caspase-3 with extender 13 to form target-extender complex 13'.

Target-extender complexes 13' and 14' were each used in the tethering method against a library of about 10,000 ligand candidates. An illustrative example of a selected ligand-candidate using target-extender complex 13' is

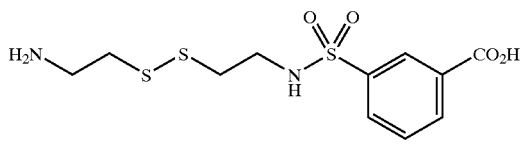

5

10 which is identical to ligand candidate 15 except that it lacks a hydroxyl group was not selected by either target-extender complexes 13' or 14'.

To assess how the extenders and the selected ligand candidates were binding to the target, two structures of the target-extender ligand conjugates were determined. General crystallographic procedures are further described in Example 12. The first structure was of the conjugate that is formed when target-extender complex 13' is contacted with ligand candidate 15. The second structure was of the conjugate that is formed when target-extender complex 14' is contacted with ligand candidate 16. Table 3 summarizes selected crystallographic data for these structures.

TABLE 3

| DATASET | SPACE GROUP | CELL [A,B,C] | RES. [Å] | COMPLETE-NESS [%] | RYSM [%] | RCRYST [%] | RFREE [%] | # MOLS/AU |
|---|---|---|---|---|---|---|---|---|
| conjugate formed from 13 and 15 | I222 | 69.49 83.60 95.60 | 20–1.6 | 95.9 | 4.3 | 17.2 | 20.5 | 1 |
| conjugate formed from 14 and 16 | P2₁2₁2₁ | 68.85 89.043 96.5 | 20–2.4 | 95.6 | 10.4 | 24.1 | 29.9 | 2 |

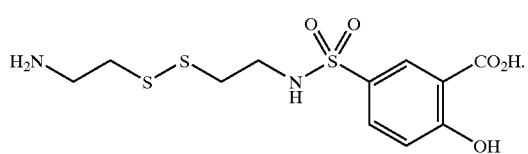

15

An illustrative example of a selected ligand candidate using target-extender complex 14' is

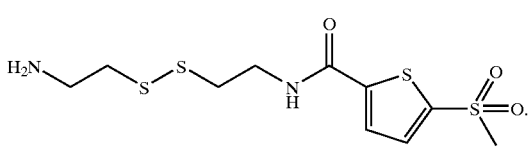

16

Notably, ligand candidate 15 was not selected by target-extender complex 14' and ligand candidate 16 was not selected by target-extender complex 13'. Structure-activity relationships among the selected compounds were also evident. For example, ligand candidate 17, Notably, the aspartic acid moiety of both extenders was superimposable with the aspartyl residue in a known tetrapeptide substrate. With respect to the binding determinant of ligand candidate 15, the salicylate sulfonamide makes numerous contacts with the protein including four hydrogen bonds. The salicylate moiety occupies the P4 pocket of the enzyme that preferentially recognizes aspartic acid in caspase-3. With respect to the binding determinant of ligand candidate 16, the sulfone makes some of the same contacts as the salicylate.

Given that the binding determinants from the extender and the ligand candidates were making productive contacts with the active site of caspase-3, compounds were designed where the disulfides were replaced with more stable linkages. In addition, derivatives were made to probe the SAR of the binding determinants. With respect to the conjugate comprising extender 13 and ligand candidate 15, the target-extender ligand conjugate comprises:

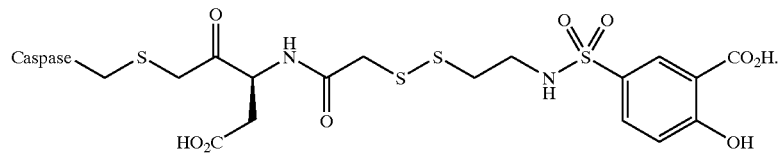
From this conjugate, a class of potent caspase-3 inhibitors was made comprising the moiety
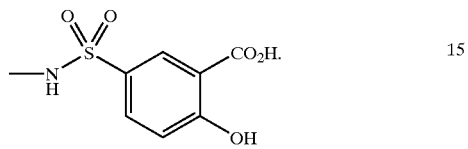
Four illustrative examples of compounds that were made based on the conjugate both for optimization and for SAR are disclosed in Table 4.
TABLE 4
| Compound | | $K_i$ ($\mu$M) |
|---|---|---|
| 18 | 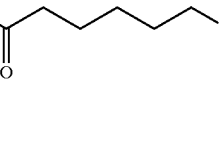 | 2.8 |
| 19 | 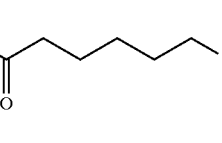 | 15.3 |
| 20 | 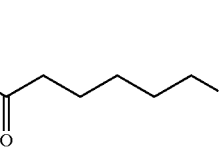 | >100 |
| 21 | 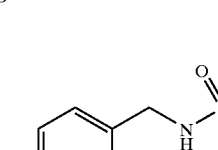 | 0.16 |
| 22 | 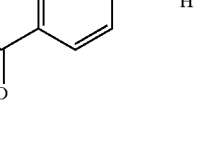 | 0.33 |

As can be seen, a conservative approach was taken wherein the two sulfur atoms were replaced with two methylene units and the arylacyloxymethylketone (first functionality) was replaced with a simple aldehyde resulting in compound 18, a potent inhibitor of caspase-3 with a $K_i$ of 2.8 μM. Removing the hydroxyl group to yield compound 19 reduced the affinity by a factor of five, confirming the SAR observed in the tether screen. Removing both the hydroxyl group and the acid moiety to yield compound 20 ablated binding affinity entirely. Modeling studies suggested that replacing the methylene linker with a rigid aminobenzyl moiety would effectively bridge the distance between the aspartyl group and the salicylate while reducing the entropic costs of the linker. Indeed, as can be seen, compound 21 has a $K_i$ that is more than 10 fold better than compound 18.

Similarly, a novel class of caspase-3 inhibitors resulted from the target-extender ligand conjugate comprising extender 14 and ligand candidate 16,

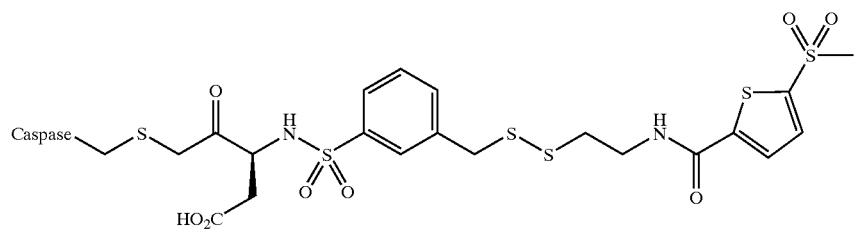

In one embodiment, the compounds comprise the moiety

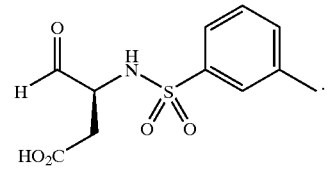

In another embodiment, the compounds are of the structure

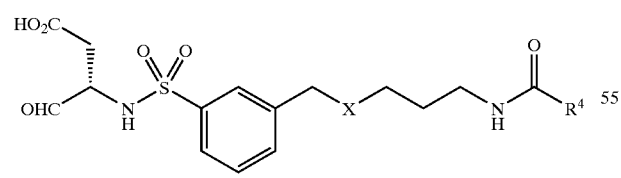

where X is $CH_2$, S, SO, $SO_2$, and $R^5$ is unsubstituted aryl or substituted aryl. In another embodiment, $R^4$ is a unsubstituted heteroaryl or substituted heteroaryl. An illustrative example of a compound of this class is compound 22 with a $K_i$ of 0.33 μM.

Examples 13 and 15–21 describe in greater detail a select number of caspase-3 inhibitors that were synthesized based upon the use of tethering using extenders 13 and 14.

The salicylate sulfonamide-containing compounds of the present invention are additionally noteworthy. The identification of salicylate sulfonamide as a suitable P4-binding fragment would not have occurred using traditional medicinal chemistry. Using compound 21 as an example, the salicylate sulfonamide-less version of compound 21 inhibits caspase-3 with a $K_i$ of approximately 28 μM. The addition of the salicylate sulfonamide to this fragment improves binding about 200 fold and results in compound 21 that has a $K_i$ of approximately 0.16 μM. In contrast, the binding affinity decreases if one uses a known tripeptide that binds to P1-P3 sites of caspase-3 such as compound I as the starting point.

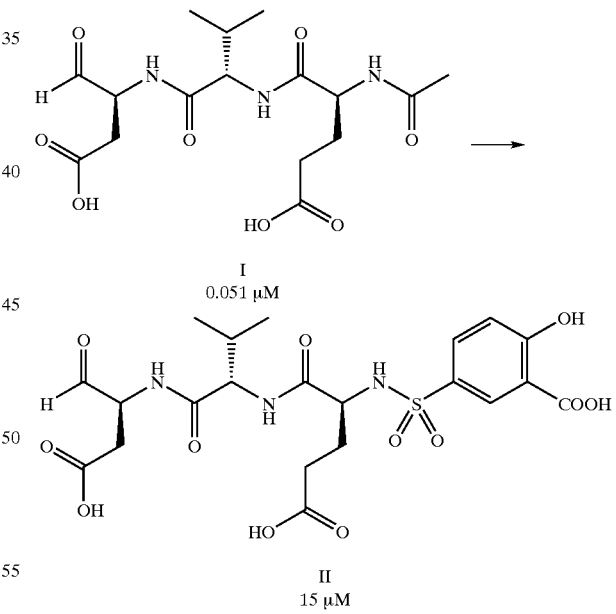

As can be seen compound I has a $K_i$ of 0.051 μM and the addition of the salicylate sulfonamide moiety to this compound yields compound II that shows about a 300 fold decrease in binding affinity. Because of this dramatic decrease, exploring P4 binding with tripeptides would not have resulted in the identification of salicylate sulfonimide as a suitable P4-binding fragment. Yet, compounds that have this fragment available for binding to P4 are potent inhibitors. Consequently, this example highlights the power of tethering to identify important fragments that may not be found using traditional methods. As shown in the case of caspase-3, these fragments can be linked together to form powerful antagonists or agonists of a target of interest.

The invention is further illustrated by the following non-limiting examples.

EXAMPLE 1

Several mutants of the unmodified or "wild-type" *E. coli* TS enzyme were created, over-expressed in *E. coli* strain χ2913 (in which the TS gene has been eliminated) and purified. The χ2913 strain requires a thymidine supplement since the (deleted) TS gene is essential for life. The first mutant is one where the active site cysteine has been replaced by serine (abbreviated as C146S). The second and third mutants include a non-native cysteine that has been introduced into the active site in addition to the C146S mutation. The second mutant includes a cysteine at residue 143 instead of a leucine and is denoted C146S/L143C. The third mutant includes a cysteine at residue 147 instead of a histidine and is denoted as C146S/H147C. Other mutants include D169C, W83C, and I79C where the active site cysteine (C146) was retained.

EXAMPLE 2

The disulfide-containing library members were made from commercially available carboxylic acids and mono-N-(tert-butoxycarbonyl)-protected cystamine (mono-BOC-cystamine) by adapting the method of Parlow and coworkers (*Mol. Diversity* 1:266–269 (1995)). Briefly, 260 μmol of each carboxylic acid was immobilized onto 130 μmol equivalents of 4-hydroxy-3-nitrobenzophenone on polystyrene resin using 1,3-diisopropylcarbodiimide ("DIC") in N,N-dimethylformamide ("DMF"). After 4 hours at room temperature, the resin was rinsed with DMF (2×), dichloromethane (DCM, 3×), and tetrahydrofuran ("THF", 1×) to remove uncoupled acid and DIC. The acids were cleaved from the resin via amide formation with 66 μmol of mono-BOC protected cystamine in THF. After reaction for 12 hours at ambient temperature, the solvent was evaporated and the BOC group was removed from the uncoupled half of each disulfide using 80% trifluoroacetic acid ("TFA") in DCM. The products were characterized by HPLC-MS, and those products which were substantially pure were used without further purification. A total of 530 compounds were made using this methodology.

Libraries were also constructed from mono-BOC-protected cystamine and a variety of sulfonyl chlorides, isocyanates, and isothiocyanates. In the case of the sulfonyl chlorides, 10 μmol of each sulfonyl chloride was coupled with 10.5 μmol of mono-BOC protected cystamine in THF (with 2% diisopropyl ethyl amine) in the presence of 15 milligrams of poly(4-vinyl pyridine). After 48 hours the poly(4-vinylpyridine) was removed via filtration and the solvent was evaporated. The BOC group was removed using 50% TFA in DCM. In the case of the iso(thio)cyanates, 10 μmol of each isocyanate or isothiocyanate was coupled with 10.5 μmol of mono-BOC-protected cystamine in THF. After reaction for 12 hours at ambient temperature, the solvent was evaporated and the BOC group was removed using 50% TFA in DCM. A total of 212 compounds were made using this methodology.

Finally, oxime-based libraries were constructed by reacting 10 μmol of specific aldehydes or ketones with 10.5 μmol of $HO(CH_2)_2SS(CH_2)_2ONH_2$ in 1:1 methanol:chloroform (with 2% acetic acid added) for 12 hours at ambient temperature to yield the oxime product A total of 448 compounds were made using this methodology.

Individual library members were redissolved in either acetonitrile or dimethylsulfoxide to a final concentration of 50 or 100 mM. Aliquots of each of these were then pooled into groups of 8–15 discreet compounds, with each member of the pool having a unique molecular weight.

EXAMPLE 3

N-tosyl-proline derivatives were synthesized as follows. Proline methyl ester hydrochloride was reacted with 4-(chlorosulfonyl)benzoic acid and sodium carbonate in water. The product was converted to the pentafluorophenyl ester by reacting it with pentafluorophenyl trifluoroacetate and pyridine in N,N-dimethylformamide, and purified via flash chromatography. This activated ester was then reacted with the methyl-ester of glutamate (or any of the other amino acids tested) in the presence of triethylamine and dichloromethane, the product purified by flash chromatography, and the methyl esters hydrolyzed with lithium hydroxide in water. The final products were purified via reverse-phase HPLC and lyophilized.

Alternatively, the above sequence was followed starting with proline t-butyl ester. After coupling of the amino ester to the benzoic acid, the t-butyl ester was removed with 50% TFA in DCM with triethylsilane as a scavenger. The free acid was then converted to a pentafluorophenyl ester as above and reacted with the appropriate amine. The methyl esters were hydrolyzed with lithium hydroxide in water, and the final products were purified via reverse-phase HPLC and lyophilized.

EXAMPLE 4

Disulfide library screening occurred as follows. In a typical experiment, 1 μl of a DMSO solution containing a library of 8–15 disulfide-containing compounds is added to 49 μl of protein-containing buffer. These compounds were chosen so that each has a unique molecular weight. Ideally, these molecular weights differ by at least 10 atomic mass units (amu) so that deconvolution is unambiguous. Although pools of 8–15 disulfide-containing compounds were typically used for ease of deconvolution, larger pools can be used. The protein is present at a concentration of ~15 μM, each of the disulfide library members is present at ~0.2 mM, and thus the total concentration of all disulfide library members is ~2 mM. Screening occurred in a buffer containing 25 mM potassium phosphate (pH 7.5) and 1 mM 2-mercaptoethanol, although other buffers and reducing agents can be used. The reactions were allowed to equilibrate at ambient temperature for at least thirty minutes. These conditions can be varied considerably depending on the ease with which the protein ionizes in the mass-spectrometer (see below), the reactivity of the specific cysteine(s), etc. In the case of TS the conditions described above were found to be satisfactory. No special effort was taken to exclude oxygen or adventitious metal ions; on the time-scale of these reactions there is sufficient free thiol to facilitate disulfide exchange.

After equilibration, the reactions were injected onto an HP1100 HPLC and chromatographed on a C18 column attached to a mass-spectrometer (Finnigan MAT LCQ). The multiply charged ions arising from the protein were deconvoluted with available software (Xcalibur) to arrive at the mass of the protein. The identity of any library member bonded through a disulfide bond to the protein was then easily determined by subtracting the known mass of the unmodified protein from the observed mass. This process assumes that the attachment of a library member does not dramatically change the ionization characteristics of the protein itself, a conservative assumption due to the fact that in most cases the protein will be at least twenty-fold larger than any given library member. This assumption was confirmed by demonstrating that small molecules selected by one protein are not selected by other proteins

EXAMPLE 5

Crystals were grown as previously described in Perry et al, *Proteins* 8: 315–333 (1990), with the exception that for the noncovalent complexes, 1 mM compound was included in the crystallization buffer. Prior to data collection, crystals were transferred to a solution containing 70% saturated $(NH_4)_2SO_4$, 20% glycerol, 50 mM $K_2HPO_4$, pH 7.0. For the non-covalent N-tosyl-D-proline complex, 10 mM compound was added to the soaking solution; for the other complexes, 1 mM compound was included. Diffraction data were collected at −170° C. using a Rigaku RU-3R generator and an R-axis-IV detector, and processed using d*TREK. As these crystals were isomorphous with previously described structures (PDB code 1TJS for the I2 13 form and 2TSC for the P6 3 form), refinement began by rigid body refinement using REFMAC (CCP4). The protein model was adjusted using a compound model constructed in INSIGHT-II (MSI, San Diego), and PROTIN (CCP4) dictionary created using MAKEDIC (CCP4). Positional and individual isotropic temperature factor refinements were carried out with REFMAC (CCP4) using all reflections in the indicated resolution ranges. Solvent molecules were placed automatically using ARPP (CCP4) and refinement continued until no interpretable features remained in Fo-Fc difference maps. PDB accession numbers are 1F4B, 1F4C, 1F4D, 1F4E, 1F4F for the native, C146-tethered N-tosyl-D-proline, L143C-tethered N-tosyl-D-proline, N-tosyl-D-proline free acid soak, glutamate-N-tosyl-D-proline soak, and glutamate-N-tosyl-D-proline-β-alanine crystals, respectively.

EXAMPLE 6

The selected N-tosyl-D-proline compound was optimized and tested as a series of ligand candidates using tethering. Based on the crystal structure of N-tosyl-D-proline bound to TS, the methyl group off the phenyl ring was in a promising location for use as a derivitization point. Scheme 1 illustrates the general method that was used to synthesize derivatives using 88 different aldehydes (where $R^5$ is selected from unsubstituted aryl or substituted aryl) and six different linkers.

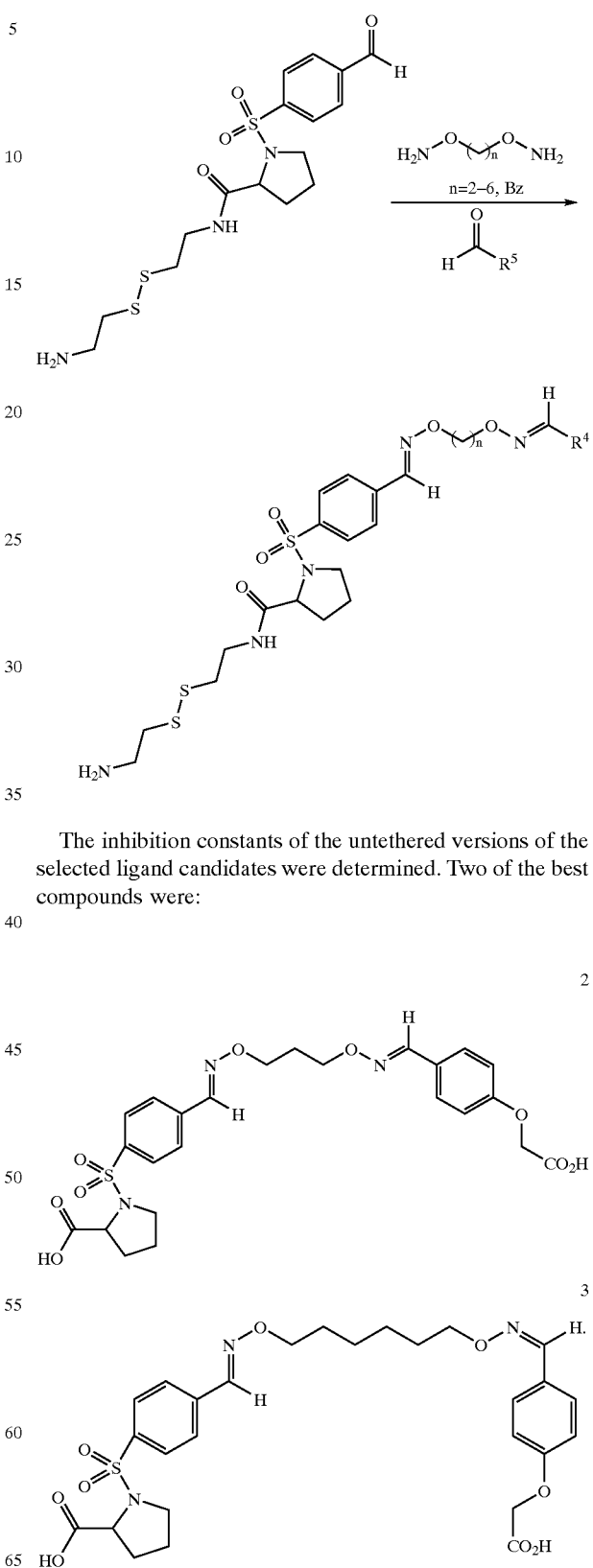

The inhibition constants of the untethered versions of the selected ligand candidates were determined. Two of the best compounds were:

The $K_i$ of compound 2 was determined to be about 55 μM and the $K_i$ of compound 3 was determined to be about 40 μM.

EXAMPLE 7

This example describes one embodiment for the synthesis of compound 13. The general reaction scheme is outlined in Scheme 2.

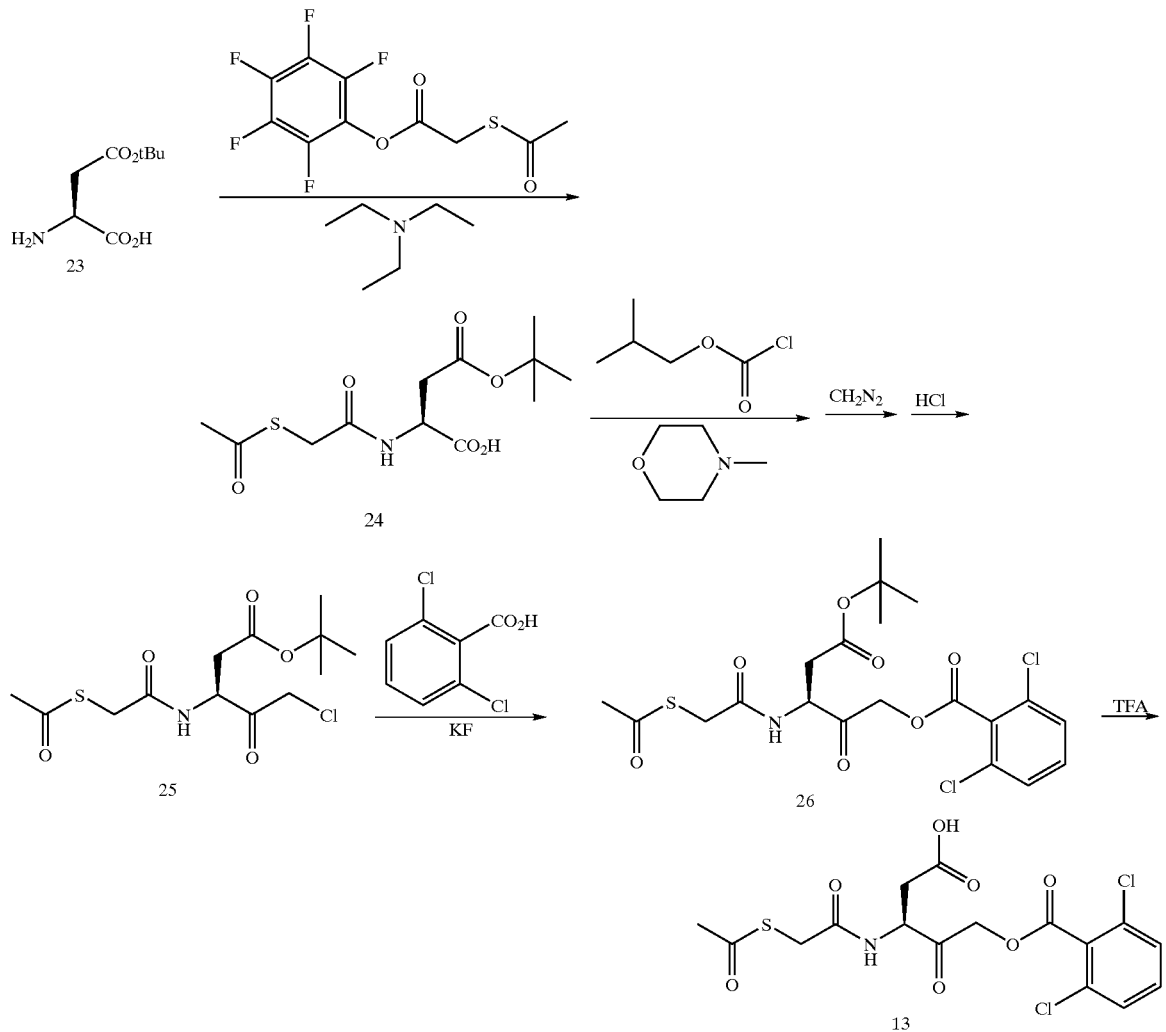

2-(2-Acetylsulfanyl-acetylamino)-succinic acid 4-tert-butyl ester 24

Acetylsulfanyl-acetic acid pentafluorophenyl ester (1.6 g, 5.3 mmol) and H-Asp(OtBu)-OH (1 g, 5.3 mmol) were mixed in 20 ml of dry dichloromethane (DCM). Then 1.6 ml of triethylamine (11.5 mmol) was added, and the reaction was allowed to proceed at ambient temperature for 3.5 hours. The organic layer was then extracted with 3×15 ml of 1 M sodium carbonate, the combined aqueous fractions were acidified with 100 ml of 1 M sodium hydrogensulfate and extracted with 3×30 ml ethyl acetate. The combined organic fractions were then rinsed with 30 ml of 1 M sodium hydrogensulfate, 30 ml of 5 M NaCl, dried over sodium sulfate, filtered, and evaporated under reduced pressure to yield 1.97 g of 24 as a nearly colorless syrup which was used without further purification. MW=305 (found 306, M+1).

3-(2-Acetylsulfanyl-acetylamino)-5-chloro-4-oxo-pentanoic acid tert-butyl ester 25

The free acid 24 was dissolved in 10 ml of dry tetrahydrofuran (THF), cooled to 0° C., and treated with 0.58 mlN-methyl-morpholine (5.3 mmol) and 0.69 ml of isobutylchloroformate. Dense white precipitate immediately formed, and after 30 minutes the reaction was filtered through a glass frit and transferred to a new flask with an additional 10 ml of THF. Meanwhile, diazomethane was prepared by reacting 1-methyl-3-nitro-1-nitrosoguanidine (2.3 g, 15.6 mmol) with 7.4 ml of 40% aqueous KOH and 25 ml diethyl ether for 45 minutes at 0° C. The yellow ether layer was then decanted into the reaction containing the mixed anhydride, and the reaction allowed to proceed while slowly warming to ambient temperature over a period of 165 minutes. The reaction was cooled to 8° C., and 1.5 ml of 4

N HCl in dioxane (6 mmol total) was added dropwise. This resulted in much bubbling, and the yellow solution became colorless. The reaction was allowed to proceed for two hours while gradually warming to ambient temperature and then quenched with 1 ml of glacial acetic acid. The solvent was removed under reduced pressure and the residue redissolved in 75 ml ethyl acetate, rinsed with 2×50 ml saturated sodium bicarbonate, 50 ml 5 M NaCl, dried over sodium sulfate, filtered, and evaporated to dryness before purification by flash chromatography using 90:10 chloroform:ethyl acetate to yield 0.747 g of 25 as a light yellow oil (2.2 mmol, 42% from 23). Expected MW=337.7, found 338 (M+1).

2,6-Dichloro-benzoic acid 3-(2-acetylsulfanyl-acetylamino)-4-tert-butoxycarbonyl-2-oxo-butyl ester 26

The chloromethylketone 25 (0.25 g, 0.74 mmol) was dissolved in 5 ml of dry N,N-dimethylformamide (DMF), to which was added 0.17 g 2,6-dichlorobenzoic acid (0.89 mmol) and 0.107 g KF (1.84 mmol). The reaction was allowed to proceed at ambient temperature for 19 hours, at which point it was diluted with 75 ml ethyl acetate, rinsed with 2 ×50 ml saturated sodium bicarbonate, 50 ml 1 M sodium hydrogen sulfate, 50 ml 5 M NaCl, dried over sodium sulfate, filtered, and dried under reduced pressure to yield a yellow syrup which HPLC-MS revealed to be about 75% product 26 and 25% unreacted 25. This was used without further purification. Expected MW=492.37, found 493 (M+1).

2,6-Dichloro-benzoic acid 3-(2-acetylsulfanyl-acetylamino)-4-carboxy-2-oxo-butyl ester 13

The product 26 was dissolved in 10 ml of dry DCM, cooled to 0° C., and treated with 9 ml trifluoroacetic acid (TFA). The reaction was then removed from the ice bath and allowed to warm to ambient temperature over a period of one hour. Solvent was removed under reduced pressure, and the residue redissoved twice in DCM and evaporated to remove residual TFA. The crude product 13 was purified by reverse-phase high-pressure liquid chromatography to yield 101.9 mg (0.234 mmol, 32% from 25) of white hygroscopic powder. Expected MW=436.37, found 437 (M+1). This was dissolved in dimethylsulfoxide (DMSO) to yield a 50 mM stock solution.

EXAMPLE 8 a. This example describes one embodiment for an extender, compound 32, that was used in tethering experiments for caspase-3. The general scheme is described in Scheme 3.

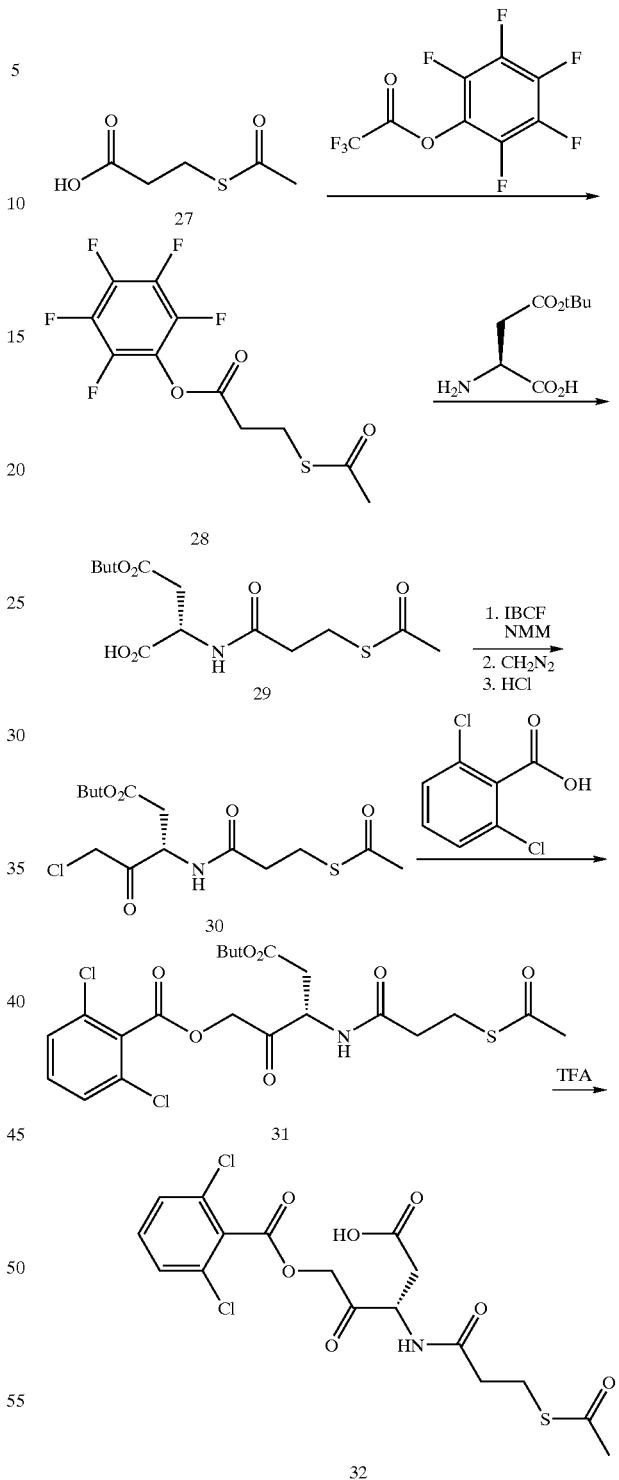

a) 3-mercaptopropionic acid (4 g, 37.69 mmol) was added under nitrogen to a degassed solution of $K_2CO_3$ (15.63 g, 113 mmol) in 125 mL deionized ("DI") water. This solution was then cooled to 0° C. and acetic anhydride (3.56 ml, 37.69 mmol) was added dropwise. The reaction was stirred for 15 minutes, washed with 2×50 mL $Et_2O$ and acidified to pH 2 with 1M HCL. The aqueous layer was then extracted with 3×25 mL ethyl acetate ("EtOAc"). The combined organic layers were washed with brine, dried over anhydrous Na₂SO₄, filtered, and the solvent removed under reduced pressure to yield compound 27 (5.19 g, 35 mmol), 93%, ES (+) MS m/e=148(M+H) which was used without further purification.

b) Compound 27 (2.36 g, 15.94 mmol) was dissolved in 50 mL dry tetrahydrofuran ("THF") and pyridine (1.35 mL, 16.74 mmol) was added followed by pentafluorophenyl trifluoroacetate (2.71 mL, 15.78 mmol). The solution was stirred at ambient temperature for 2 hours. The THF was removed under reduced pressure and the residue redissolved in 75 mL EtOAc, washed with 2×25 mL 1M HCl, 25 mL saturated NaHCO₃, 25 mL brine, dried over anhydrous Na₂SO₄, filtered, and the solvent removed under reduced pressure to yield compound 28 (3.77 g, 12 mmol, 75%), ES (+) MS m/e=314(M+H) which was used without further purification.

c) Compound 28 (3.77 g, 11.99 mmol) was mixed with H₂N-Asp(OtBu)-CO₂H (2.27 g, 11.99 mmol) and suspended in 40 mL dry DCM. Then triethylamine (2.9 ml, 20.8 mmol) was added and the solution stirred for 16 hours at which point it was flooded with 100 mL EtOAc, rinsed with 2×50 mL 1 M NaHSO₄ and 50 mL brine, dried over anhydrous Na₂SO₄, filtered, and the solvent removed under reduced pressure to yield product which was purified by flash chromatography using 94:5:1 CHCl₃:methanol:acetic acid yielding compound 29 (2.62 g, 8.2 mmol, 68% yield, ES (+) MS m/e=264 ((M−tBu)+H)).

d) Compound 29 (2.62 g, 8.2 mmol) was dissolved in 25 mL dry THF and cooled to 0° C. To this solution was added N-methylmorpholine (1.88 mL, 17.06 mmol) followed by isobutyl chloroformate (2.15 mL, 16.56 mmol). The resulting suspension was allowed to stir for an additional 2 hours and the mixture filtered. This solution was poured into an ethereal diazomethane solution at 0° C. The deep yellow solution was allowed to warm to room temperature overnight. Nitrogen was bubbled through the deep orange solution for 30 minutes. One half of the of the solution was cooled to 0° C. and 4M HCl (3.8 mL, 15 mmol) was added dropwise and the solution stirred at 0° C. for 1 hour. The solvent was removed under reduced pressure and the residue redissolved in 50 mL EtOAc. The organic layer was washed with 2×25 mL saturated NaHCO₃, 25 mL brine, dried over anhydrous Na₂SO₄ and concentrated and was purified by flash chromatography using 95:5 CHCl₃:EtOAc, yielding compound 30 (0.198 g, 0.562 mmol, 14%), ES (+) MS m/e=296 ((M−tBu)+H)).

e) Compound 30 (50 mg, 0.143 mmol) was dissolved in 1 ml dry dimethylformamide ("DMF"), and added to a mixture of 2,6-dichlorobenzoic acid (33 mg, 0.172 mmol) and KF (21 mg, 0.358 mmol). The solution was stirred at ambient temperature for 16 hours, then flooded with 20 mL EtOAc, rinsed with 2×10 mL saturated NaHCO₃, 10 mL brine, dried over anhydrous Na₂SO₄, filtered, and the solvent removed under reduced pressure to yield compound 31 (48 mg, 0.098 mmol, 67%), ES (+) MS m/e=451 ((M−tBu)+H)).

f) Compound 31 was dissolved in 5 mL dichloromethane ("DCM") and cooled to 0° C., 5 mL trifluoroacetic acid ("TFA") was added and the solution stirred for 30 minutes. The solvent was removed under reduced pressure and the crude residue was purified by reverse-phase preparatory HPLC to afford compound 32 (0.006 g, 0.013 mmol, 14%) ES (+) MS: m/e=450.29 (M+1).

EXAMPLE 9

This example describes one embodiment for the synthesis of compound 14. The general reaction scheme is outlined in Scheme 4

SCHEME 4

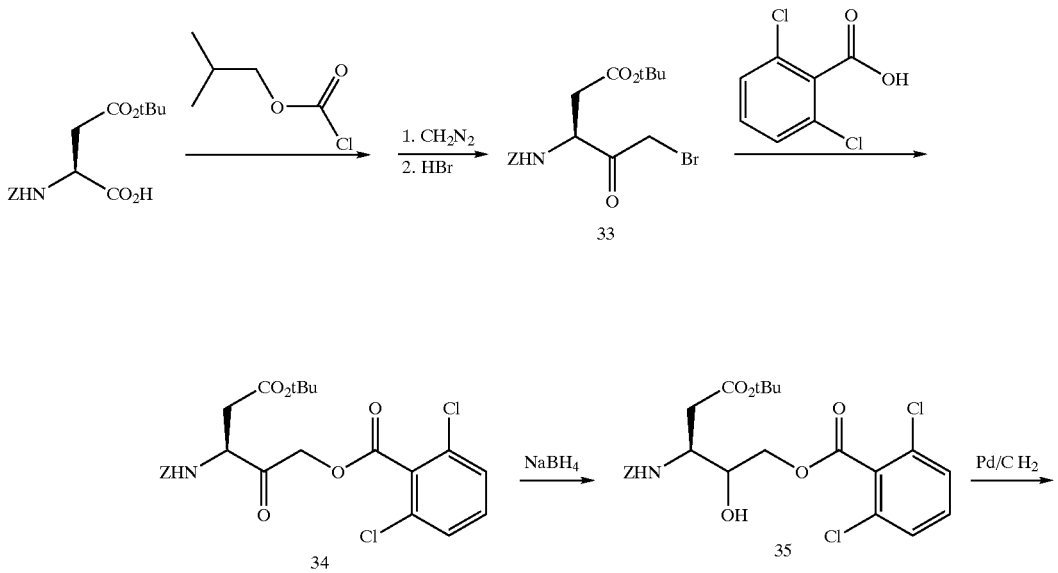

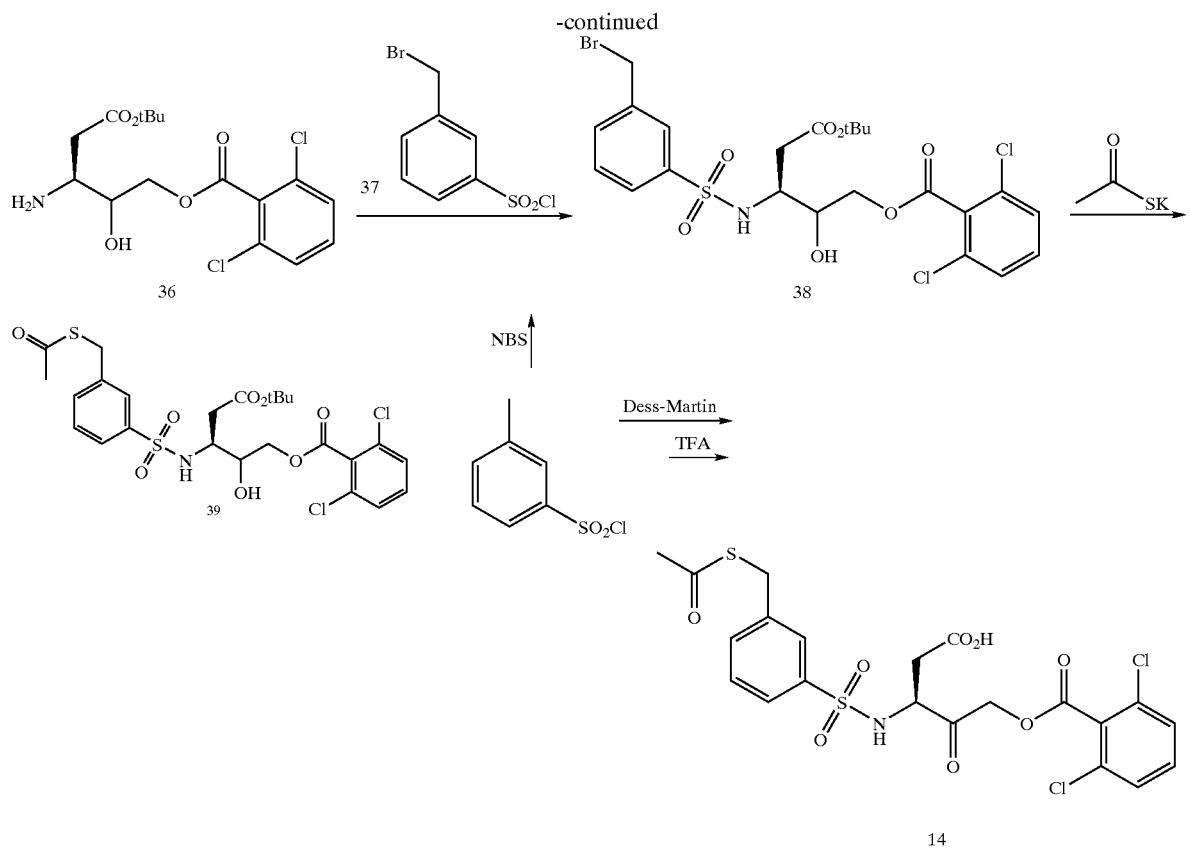

a) Z-ASP(OtBu)-OH was used to give compound 33 analogously to compound 30 of Example 8. ES (+) MS m/e=344 ((M−tBu)+H)).

b) Compound 34 was prepared according to procedure of Example 8e except starting with compound 33 instead of compound 30 (88%). ES (+) MS m/e=454 ((M−tBu)+H)).

c) Compound 34 (0.5 g, 0.9 mmol) was dissolved in 10 mL MeOH and cooled to 0° C. Then NaBH$_4$ (0.074 g, 1.96 mmol) was added in portions and the reaction stirred for 1.5 hours. The reaction was flooded with 25 mL 1M HCl and extracted with 3×10 mL DCM, dried over anhydrous Na$_2$SO$_4$, filtered, and the solvent removed under reduced pressure to yield compound 35 (0.297 g, 0.058 mmol, 60%), ES (+) MS m/e=456 ((M−tBu)+H)).

d) Compound 35 (0.297 g, 0.579 mmol) was dissolved in 5 mL MeOH, the solution was then sparged with nitrogen, wet Pd/C (10% weight/weight, Aldrich, 0.123 g) was added, and the solution was stirred under a balloon filled with hydrogen for 30 minutes. The reaction was then filtered through Celite, and the solvent removed under reduced pressure to yield compound 36 (0.188 g, 0.497 mmol, 86%), ES (+) MS m/e=292 ((M−tBu)+H)).

e) A solution of meta-toluenesulfonyl chloride (6.8 g, 35.67 mmol), N-bromosuccinimide (6.35 g, 35.67 mmol), and benzoyl peroxide (0.670 g, 3.07 mmol) in 40 mL CCl$_4$ was refluxed for 2 h. After cooling to room temperature, the mixture was filtered, the solvent removed under reduced pressure and the product purified by flash chromatography using 9.5:0.5 Hexanes:EtOAc yielding compound 37 (3.43 g, 12.7 mmol, 36%), ES (+) MS m/e=213 ((M−)+H)).

f) Compound 36 (0.188 g, 0.497 mmol) was dissolved in 2 mL DCM and diisopropylethylamine (0.173 mL, 0.994 mmol) was added, this solution was then added dropwise to compound 37 (0.670 g, 2.49 mmol) dissolved in 20 mL DCM. After stirring at room temperature for 20 minutes, the DCM was removed under reduced pressure and the residue redissolved in 20 mL EtOAc, rinsed with 2×10 mL 1 M NaHSO$_4$, 10 mL saturated NaHCO$_3$, 10 mL brine, dried over anhydrous Na$_2$SO$_4$, filtered, and the solvent removed under reduced pressure to yield product which was purified by flash chromatography using 4:1 Hexanes:EtOAc yielding compound 38 (0.068 g, 0.111 mmol, 22%), ES (+) MS m/e=555 ((M−tBu)+H)).

g) Compound 38 (0.068 g, 0.111 g) was dissolved in 1 mL DMF and potassium thioacetate (0.013 g, 0.111 mmol) was added. The reaction was stirred for 1 hour at ambient temperature and then flooded with 10 mL DCM, washed with 2×5 mL 1 M NaHSO$_4$, 5 mL saturated NaHCO$_3$, and 5 mL brine, dried over anhydrous Na$_2$SO$_4$, filtered, and the solvent removed under reduced pressure to yield compound 39 (0.044 g, 0.073 mmol, 66%), ES (+) MS m/e=550 ((M−tBu)+H)).

h) Compound 39 (0.044 g, 0.073 mmol), was dissolved in 2 mL DCM and Dess-Martin periodinane (0.046 g, 0.108 mmol) was added. The reaction was stirred at room temperature for 30 minutes and the reaction filtered. 5 mL of DCM was added and the solution cooled to 0° C. before adding 7 mL TFA. The reaction was stirred for 30 minutes and the solvent removed under reduced pressure. The crude residue was purified by reverse-phase preparatory HPLC to afford compound 14. (0.005 g, 0.008 mmol, 11%) ES (+) MS: m/e=548.41 (M+1).

EXAMPLE 10

This example describes one embodiment for the synthesis of extender 40 for use in tethering with caspase-3 wherein the thiol is directed towards the prime side of the enzyme. The general reaction scheme is outlined in Scheme 5.

SCHEME 5

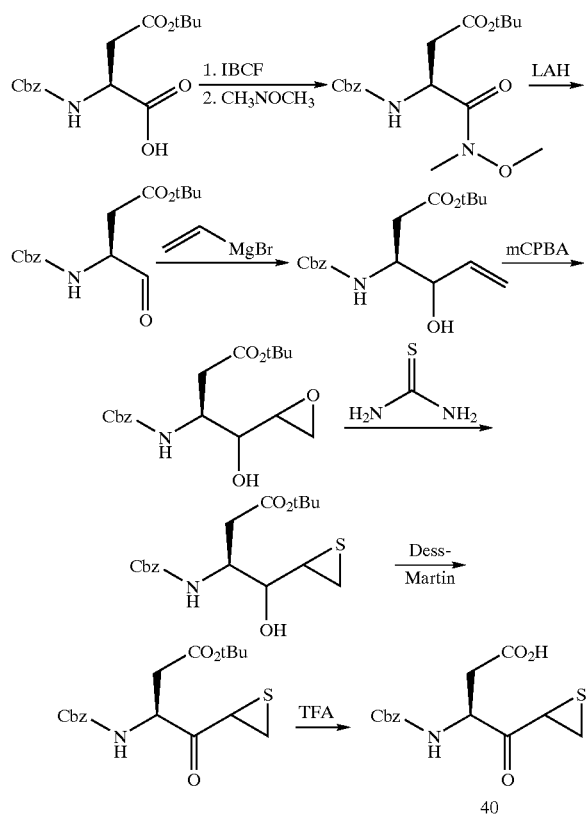

40

Cbz-Asp(OtBu)—OH (7.778 g, 24.1 mmol) was dissolved in 65 ml THF, chilled in an ice-water bath, and N-methyl-morpholine (2.6 ml, 23.6 mmol) and isobutylchloroformate (3.1 ml, 23.9 mmol) were added. The reaction was allowed to stir on ice for 20 minutes. Meanwhile, N,O-dimethylhydroxylamine hydrochloride (3.51 g, 36 mmol) and potassium carbonate (7 g, 51 mmol) was suspended in 24 ml THF and 1 ml water, stirred vigorously at ambient temperature for 20 minutes, and then filtered through filter paper directly into the carbonate solution above, followed by 20 ml THF. After 40 minutes the reaction was flooded with 200 ml EtOAc, rinsed with 3×75 ml 1 N HCl, 75 ml saturated sodium hydrogen carbonate, and 75 ml brine, dried over sodium sulfate, filtered, and evaporated to a colorless syrup which was used without further purification (9 g, 24.1 mmol, 100%, ES (+) MS m/z=389 (M+Na)).

The amide (8.8 g, 24 mmol) was dissolved in dry THF (100 ml), chilled in an ice-brine bath under nitrogen to −5 degrees C., and 1 M lithium aluminum hydride in THF (12 ml, 12 mmol) was added over the course of 10 minutes. The reaction was allowed to stir on ice for 40 minutes, then 75 ml saturated sodium hydrogen sulfate and 250 ml diethyl ether were added and stirred on ice for 15 minutes. The ether layer was removed and dried over sodium sulfate, filtered, and evaporated to yield the aldehyde which was used without further purification (8.3 g, 24 mmol, 100%, ES (+) MS m/z=348 (M+Na+H$_2$O)).

The aldehyde (8.3 g, 24 mmol) was dissolved in dry THF (100 ml), chilled in a dry-ice/acetone bath, and 1 M vinyl-magnesium bromide in THF (30 ml, 30 mmol) was added. After 1 hour another 20 ml of Grignard was added, followed by another 20 ml after 2 hours. After 4 hours the reaction was allowed to warm to ambient temperature and allowed to proceed for 90 minutes, at which point it was cooled in an ice-water bath, 100 ml of saturated sodium hydrogen sulfate was added, the aqueous layer was drained, and the organic layer rinsed with 75 ml 1 N HCl, 75 ml saturated sodium bicarbonate, and 75 ml brine, dried over sodium sulfate, evaporated to dryness, and purified on silica gel using flash chromatography first with 80:20 hexane:EtOAc, then 70:30 hexane:EtOAc to yield product alcohol (2.5 g, 7.45 mmol, 31%, ES (+) MS m/z=358 (M+Na)).

The alcohol (2.5 g, 7.45 mmol) was dissolved in dry DCM (40 ml), chilled in an ice-water bath, and treated with meta-chloroperxoybenzoic acid (mCPBA, 10 g, 44.6 mmol) and another 40 ml dry DCM. The reaction was allowed to proceed for 19 hours, at which point 75 ml saturated sodium bicarbonate was added along with another 100 ml DCM. The aqueous layer was drained, and the organic layer rinsed with 75 ml saturated sodium bicarbonate, 2×100 ml 20% saturated sodium bicarbonate, 75 ml brine, dried over sodium sulfate, filtered, evaporated to dryness, and purified by using flash chromatography using first 70:30 hexane:EtOAc, then 50:50 hexane:EtOAc to obtain product epoxide (0.828 g, 2.36 mmol, 32%, ES (+) MS m/z=352 (M+H)).

The epoxide (0.132 g, 0.376 mmol) was dissolved in dry methanol (2 ml) to which was added thiourea (52.3 mg, 0.687 mmol) and 3 ml more methanol. The reaction was then sparged and kept under nitrogen for two days. The reaction was then flooded with 50 ml EtOAc, rinsed with 2×25 ml 1 M sodium hydrogen sulfate, 2×25 ml sodium bicarbonate, 25 ml brine, dried over sodium sulfate, filtered, evaporated to dryness, and purified by flash chromatography using first 80:20 hexane:EtOAc and then 70:30 hexane:EtOAc to obtain product thiirane (35 mg, 0.095 mmol, 25%, ES (+) MS m/z=390 (M+Na)).

The thiirane (35 mg, 0.095 mmol) was dissolved in dry DCM (0.5 ml) and Dess-Martin periodinane (43.3 mg, 0.102 mmol) was added, followed by another 0.5 ml dry DCM. After 30 minutes the reaction was diluted with 7 ml DCM, filtered through a 0.45 μm filter, and purified by flash chromatography with 80:20 hexane:EtOAc to yield product (17 mg, 0.047 mmol, 49%, ES (+) MS m/z=388 (M+Na)).

The thiirane (17 mg, 0.047 mmol) was dissolved in dry DCM (5 ml), chilled in an ice-water bath, and treated with 5 ml trifluoroacetic acid. The reaction was allowed to proceed on ice for 40 minutes at which point it was evaporated to dryness and purified using reverse phase HPLC to yield compound 40 as a white solid (1.8 mg, 0.0058 mmol, 13%, ES (+) MS m/z=332 (M+Na)). This material is not stable in DMSO but is stable for months as a solution in methanol kept at −20 degrees C. It is generally preferred that the conjugation reaction of this extender to the active site thiol of caspases is performed for only 2–5 minutes at pH 6 and at low stoichiometries with respect to enzyme (1–3 equivalents)

EXAMPLE 11

This example describes the modification of caspase-3 with extender 13. Caspase-3 was cloned, overexpressed, and purified using standard techniques. To 2 ml of a 0.2 mg/ml solution was added 10 μl of 50 mM compound 13, and the reaction was allowed to proceed at ambient temperature for 3.5 hours, at which point mass-spectroscopy revealed complete modification of the caspase 3 large subunit (MW 16861, calculated 16860). The thioester was deprotected by adding 0.2 ml of 0.5 M hydroxylamine buffered in PBS buffer, and allowing the reaction to proceed for 18 hours, at which point the large subunit had a mass of 16819 (16818 calculated). The protein was concentrated in a Ultrafree 5 MWCO unit and the buffer exchanged to 0.1 M TES pH 7.5 using a Nap-5 column.

EXAMPLE 12

Crystals of caspase-3 were grown at 20° C. using the hanging drop vapor diffusion method. Equal volumes of protein solution (5–10 mg/ml of previously modified protein in 10 mM Tris pH 8.5) were mixed with the reservoir solution containing 100 mM sodium citrate, pH 5.9, 4% Glycerol, 10–20% PEG6000 and 10 mM DTT. Small rhombic plates usually appeared after 1 to 2 weeks. They reached their maximum size of approximately 200×200×20 μm after 2 months. Before data collection, crystals were dipped briefly into reservoir solution containing 25% glycerol and then flash frozen in liquid nitrogen.

Diffraction data for the two tethered compounds were collected at 100K using a Rigaku (Tokyo) RU-3R generator, an R-axis-IV detector, and processed using D*Trek. The structures were solved by molecular replacement as implemented in the program AmoRe (Navaza, J., *Acta Crystallogr. Sect. A, A*50:157–163 (1994)) using the coordinates of the Protein Data Bank entry 1CP3. Compound models were constructed in Pymol (DeLano, W. L., *World Wide Web URL*: http://www.pymol.org), the models were adjusted using program O (Jones, T. A., et al., *Acta Cryst.*, A47: 110–119 (1991)) and refined using program Refmac (CCP4).

EXAMPLE 13

This example describes one embodiment for the synthesis of compound 50. The general reaction scheme is outlined in Scheme 6.

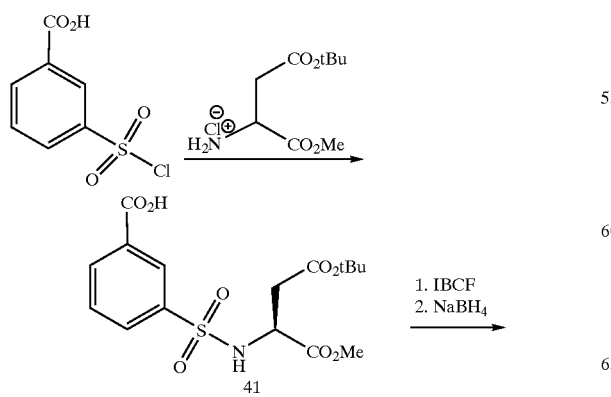

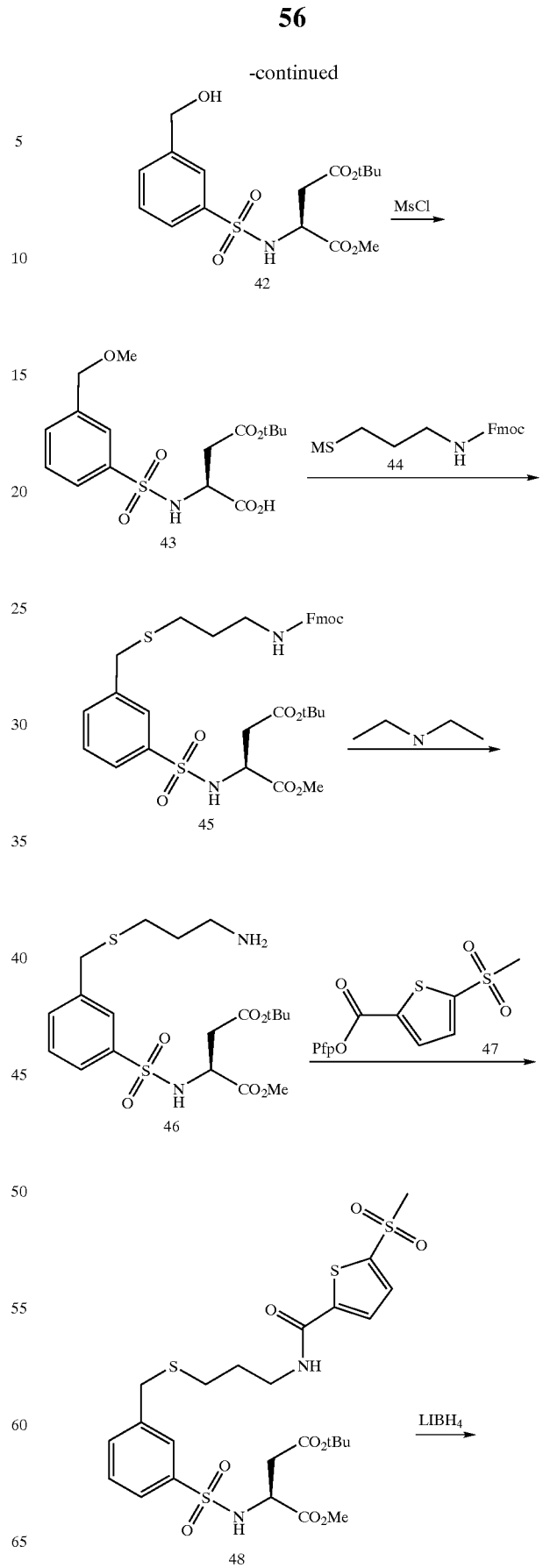

-continued

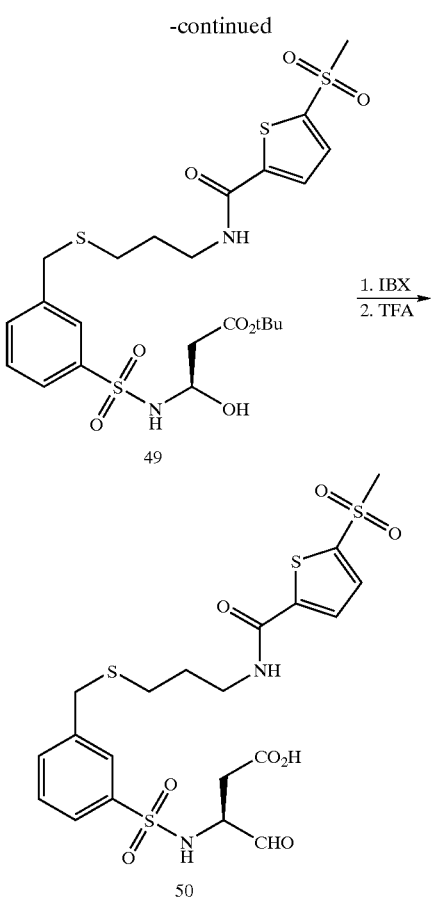

a) 3-(Chlorosulfonyl) benzoic acid (10.38 g, 47.04 mmol) was mixed with H-ASP(OtBu)-OMe (10.25 g, 42.76 mmol) and sodium carbonate (14.05 g, 133 mmol) in 500 mL DI water and the reaction stirred at room temperature for 16 hours. The solution was filtered and then acidified with 1 M NaHSO$_4$ to pH 2. The aqueous solution was extracted with 3×300 mL EtOAc. The combined organic layers were then washed with 250 mL brine, dried over anhydrous Na$_2$SO$_4$, filtered, and the solvent removed under reduced pressure to yield compound 41 (7.07 g, 18.25 mmol, 39%), ES (+) MS m/e=331 ((M−tBu)+H)) which was used without further purification.

b) Compound 41 (7.07 g, 18.25 mmol) was suspended in 90 ml dry THF under a nitrogen atmosphere and cooled to 0° C. Isobutyl chloroformate (2.49 ml, 19.16 mmol) was added via syringe followed by N-methylmorpholine (2.21 mL, 20 mmol) The reaction was stirred at 0° C. for 30 minutes, then poured into a −78° C. solution of sodium borohydride (2.4 g, 63.88 mmol) in 182 mL THF and 63 mL mL MeOH. The reaction was stirred at −78° C. for 2 hours and then most of the THF removed under reduced pressure. The residue was flooded with 200 mL EtOAc, rinsed with 2×75 mL 1M NaHSO$_4$, 75 ml saturated NaHCO$_3$, and 75 ml brine, dried over anhydrous Na$_2$SO$_4$, filtered, and the solvent removed under reduced pressure to yield compound 42 (6.80 g, 18.21 mmol, 100%), ES (+) MS m/e=317((M−tBu)+H)) as a white solid which was used without further purification.

c) Compound 42 (6.80 g, 18.21 mmol) was dissolved in 100 ml dry DCM under a nitrogen atmosphere and the solution cooled to 0° C. Triethylamine (5.34 mL, 38.33 mmol) was added followed by dropwise addition of methanesulfonyl chloride (1.55 mL, 20.08 mmol). The reaction was stirred at 0° C. for 1 hour, then rinsed with 2×35 mL 1 M NaHSO$_4$, 40 mL brine, dried over anhydrous Na$_2$SO$_4$, filtered, and the solvent removed under reduced pressure. The residue was purified by flash chromatography using 3:2 Hexanes:EtOAc to yield compound 43 (6.69 g, 14.82 mmol, 83%), ES (+) MS m/e=395 ((M−tBu)+H)).

d) Compound A was prepared according to the method of Example 13c except starting from Fmoc-β-alaninol (5.14 g, 17.29 mmol) instead of compound 42 (93%) as shown below

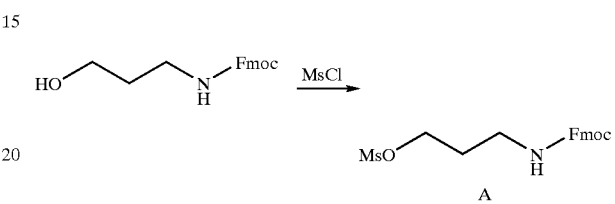

ES (+) MS m/e=375 (M+1) It was used without further purification.

e) Compound B was prepared according to the method of Example 9g except starting from compound A instead of compound 38 (91%) as shown below

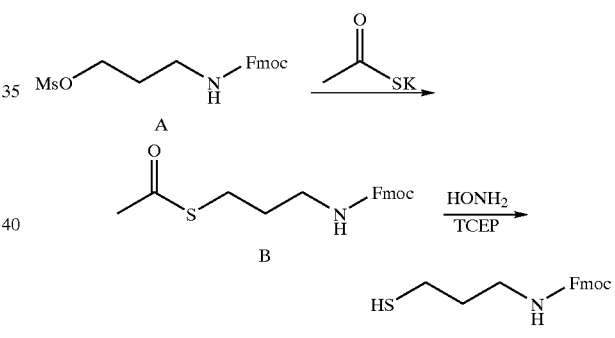

ES (+) MS m/e=355 (M+1) It was used without further purification.

f) Compound B (5.12 g, 14.4 mmol) was dissolved in 10 mL DCM and 50 mL MeOH was added. Nitrogen was bubbled through the solution for 15 minutes and then hydroxylamine (50% in water, 4.42 mL, 72 mmol) was added followed by TCEP (4.13 g, 14.4 mmol) and the reaction stirred under a nitrogen atmosphere for 4 hours. The solvent was then removed under reduced pressure and the residue redissolved in 100 mL EtOAc, washed with 50 mL saturated NaHCO$_3$, and 50 mL brine, dried over anhydrous Na$_2$SO$_4$, and filtered. The solvent was removed under reduced pressure and the residue purified by flash chromatography using 4:1 Hexanes:EtOAc to yield compound 44 (3.32 g, 10.6 mmol, 74%), ES (+) MS m/e=313 (M+1).

g) Compound 43 (2.29 g, 5.07 mmol) was dissolved in 25 mL DMF, potassium iodide (1.68 g, 10.15 mmol) was added and the mixture stirred at room temperature for 15 minutes.

Compound 44 (1.59 g, 5.07 mmol) was added followed by sodium bicarbonate (0.426 g, 5.07 mmol). The reaction was purged with nitrogen and stirred at ambient temperature for 20 hours. The reaction was then flooded with 100 mL EtOAc, rinsed with 2×50 mL 1 M $NaHSO_4$, 50 mL saturated $NaHCO_3$, and 50 mL brine, dried over anhydrous $Na_2SO_4$, filtered, and the solvent removed under reduced pressure to yield product which was purified by flash chromatography using $CHCl_3$:2M NH3 in MeOH 95:5, yielding compound 45 (1.38 g, 2.06 mmol, 41% yield), ES (+) MS m/e=612 ((M−tBu)+H)).

h) Compound 45 (1.38 g, 2.06 mmol) was dissolved in 10 mL DCM. Then 10 mL diethylamine was added. The reaction was stirred at ambient temperature for 16 hours, the solvent removed under reduced pressure and the residue purified by flash chromatography using $CHCl_3$:2M $NH_3$ in MeOH 95:5, yielding compound 46 (0.723 g, 1.62 mmol, 79% yield), ES (+) MS m/e=390 ((M−tBu)+H)).

i) Compound 47 was prepared according to the procedure of Example 8b except starting with 5-(Methanesulphonyl) thiophene-2-carboxylic acid instead of compound 27 (97%). ES (+) MS m/e=372 (M+H).

j) Compound 46 (0.320 g, 0.717 mmol) was dissolved in 5 mL DCM, compound 47 (0.401 g, 1.08 mmol) was added followed by DIEA (0.249 mL, 1.43 mmol). The reaction was stirred at ambient temperature for 16 hours and the solvent removed under reduced pressure. The residue was redissolved in 20 mL EtOAc, washed with 2×5 mL 1 M $NaHSO_4$, 5 mL brine, dried over anhydrous $Na_2SO_4$, filtered, and the solvent removed under reduced pressure to yield product which was purified by flash chromatography using DCM:EtOAc 4:1, yielding compound 48 (0.126 g, 0.198 mmol, 28% yield), ES (+) MS m/e=578 ((M−tBu)+H)).

k) Compound 48 (0.062 g, 0.098 mmol) was dissolved in 0.5 mL dry THF. To this solution was added lithium borohydride (0.003 g, 0.121 mmol) in 1 mL ethyl ether. The reaction was stirred at room temperature for 45 minutes and then flooded with 10 mL EtOAc, rinsed with 5 mL saturated $NaHCO_3$, and 5 mL brine, dried over anhydrous $Na_2SO_4$, filtered, and the solvent removed under reduced pressure to yield compound 49 (0.058 g, 0.0096 mmol, 98%), ES (+) MS m/e=550 ((M−tBu)+H)).

l) Compound 49 (0.058 g, 0.098 mmol) was dissolved in 1 mL DMSO and IBX was added (0.082 g, 0.294 mmol). The reaction was stirred at ambient temperature for 5 hours and then flooded with 10 mL EtOAc, washed with 5 mL saturated $NaHCO_3$, and 5 mL brine, dried over anhydrous $Na_2SO_4$, filtered, and the solvent removed under reduced pressure to yield a yellow solid which was then dissolved in 5 mL DCM and cooled to 0° C. 5 mL of TFA was added and the reaction stirred for 30 minutes. After removal of solvent under reduced pressure the crude residue was purified by reverse-phase preparatory HPLC to afford compound 50 (0.009 g, 0.016 mmol, 17%) ES (+) MS: m/e=548.68 (M+1).

EXAMPLE 14

This example describes one embodiment for the synthesis of compound 51 which is shown below

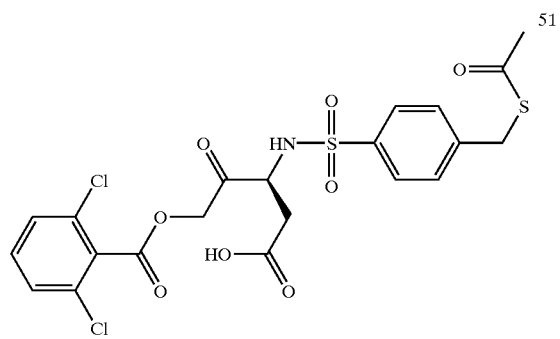

Compound 51 was prepared according to the procedure of Example 9 a–h except substituting para-tolunenesulfonyl chloride for meta-toluenesulfonyl chloride. ES (+) MS: m/e=548.41 (M+1).

EXAMPLE 15

This example describes one embodiment for the synthesis of compound 54. The general reaction scheme is outlined in Scheme 7.

SCHEME 7

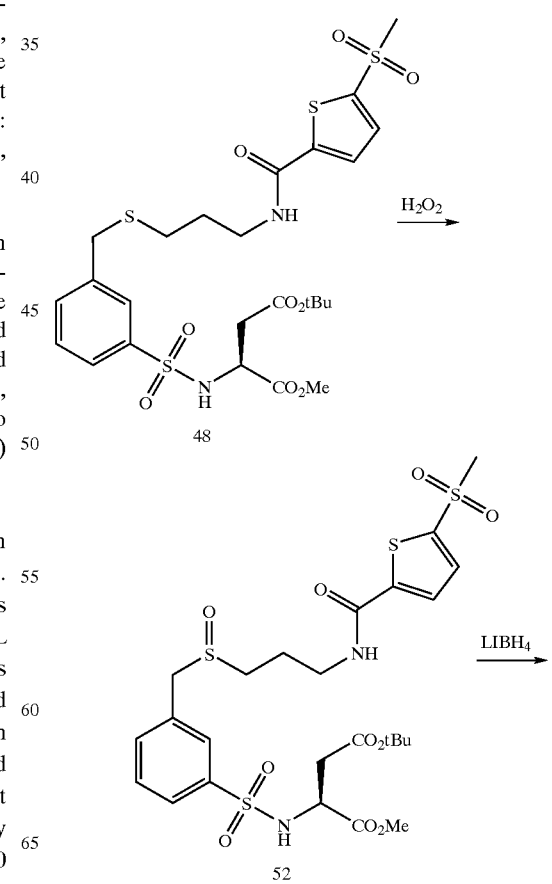

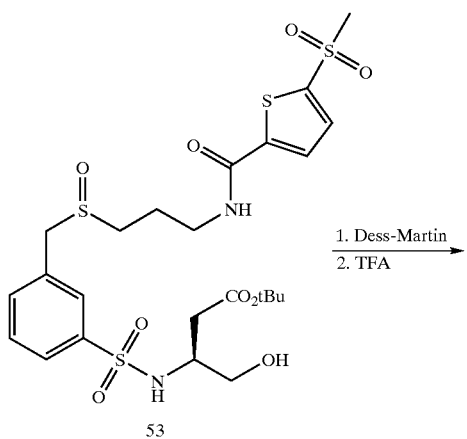

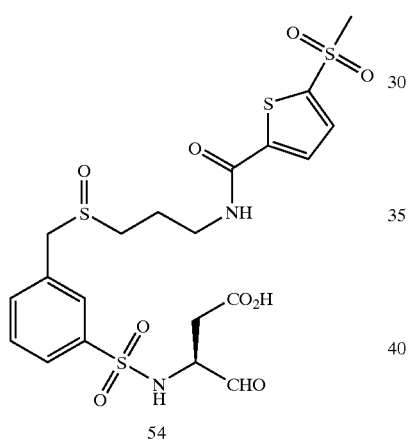

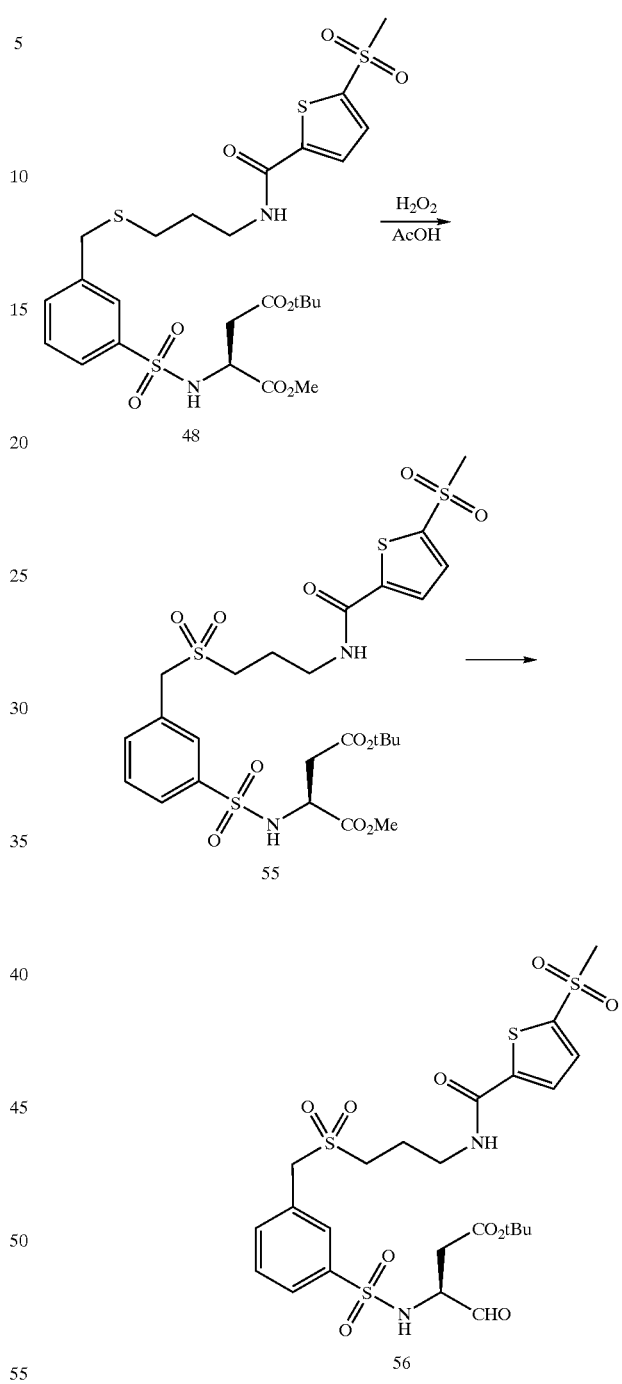

SCHEME 8 a) Compound 48 (0.063 g, 0.099 mmol) was dissolved in 5 mL MeOH and hydrogen peroxide (0.026 mL, 0.297 mmol, 30% in water) was added. The reaction was heated to 50° C. for 16 hours and the solvent removed under reduced pressure to yield compound 52 (0.063 g, 0.097 mmol, 98%), ES (+)MS m/e=594 ((M−tBu)+H)).

b) Compound 53 was prepared according to the procedure of Example 13k except substituting compound 52 for compound 48 ES (+) MS m/e=566 ((M−tBu)+H)).

c) Compound 54 was prepared according to the procedure of Example 9h except substituting compound 53 for compound 39 (0.005 g, 0.009 mmol, 11%), ES (+) MS m/e=564.68 (M+1).

EXAMPLE 16

This example describes one embodiment for the synthesis of compound 56. The general reaction scheme is outlined in Scheme 8.

a) Compound 48 (0.150 g, 0.236 mmol) was dissolved in 5 mL MeOH, acetic acid (5 mL)was added followed by hydrogen peroxide (0.77 mL, 10 mmol, 35% in water). The reaction was heated to 80° C. for 16 hours and the solvent removed under reduced pressure to yield compound 55 (0.157 g, 0.236 mmol, 100%), ES (+) MS m/e=610 ((M−tBu)+H)).

b) Compound 56 was prepared according to the procedure of Example 13k followed by Example 9h except starting with compound 55 (0.005 g, 0.0086 mmol, 36%), ES (+) MS m/e=580 (M+1).

EXAMPLE 17

This example describes one embodiment for the synthesis of compound 57 which is shown below

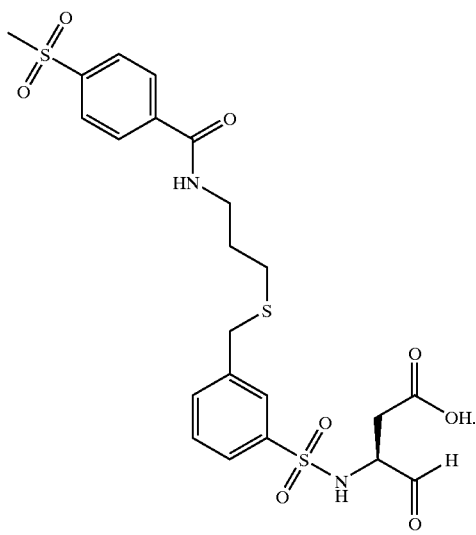

Compound 57 was prepared according to the procedure of Example 13a–l except substituting 4-(methylsulfonyl)benzoic acid for 5-(methanesulphonyl)thiophene-2-carboxylic acid. ES (+) MS: m/e=543 (M+1).

EXAMPLE 18

This example describes one embodiment for the synthesis of compound 58 which is shown below

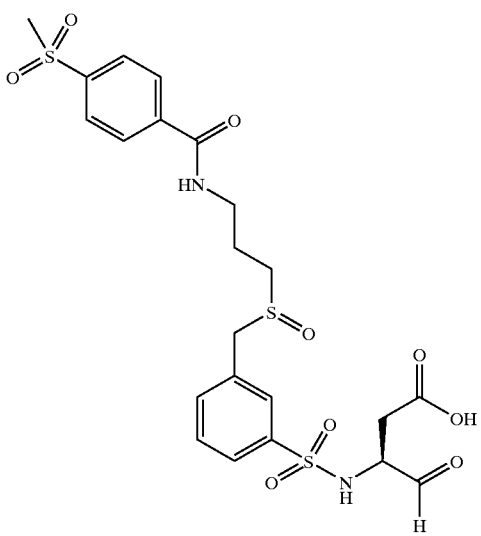

Compound 58 was prepared according to the procedure of Example 13a–j except substituting 4-(methylsulfonyl)benzoic acid for 5-(methanesulphonyl)thiophene-2-carboxylic acid followed by the procedure of Example 15a–c. ES (+) MS: m/e=559 (M+1).

EXAMPLE 19

This example describes one embodiment for the synthesis of compound 59 which is shown below.

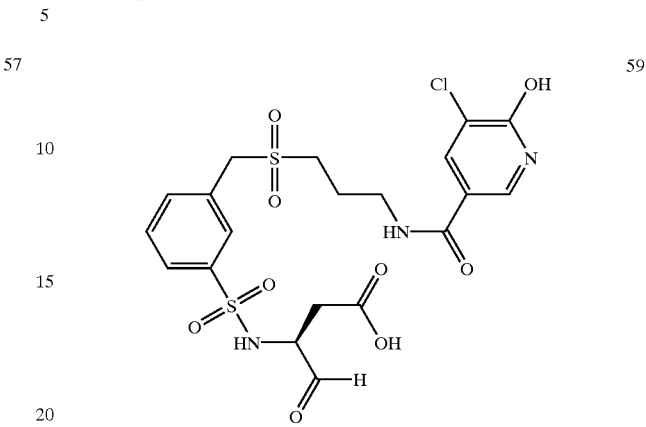

Compound 59 was prepared according to the procedure of Example 13a–j except substituting 45-chloro-6-hydroxynicotinic acid for 5-(methanesulphonyl) thiophene-2-carboxylic acid followed by the procedure of Example 16a–b. ES (+) MS: m/e=548 (M+1).

EXAMPLE 20

This example describes one embodiment for the synthesis of compound 60 which is shown below

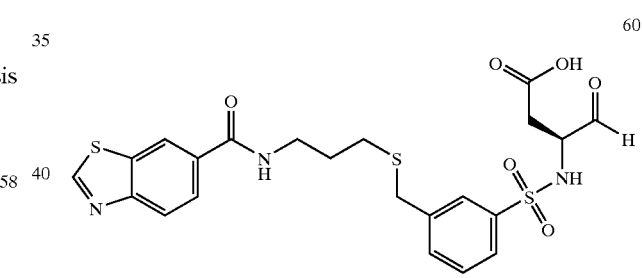

Compound 60 was prepared according to the procedure of Example 13a–l except substituting benzothiazole-6-carboxylic acid for 5-(methanesulphonyl)thiophene-2-carboxylic acid. ES (+)MS: m/e=522 (M+1).

EXAMPLE 21

This example describes one embodiment for the synthesis of compound 61 which is shown below

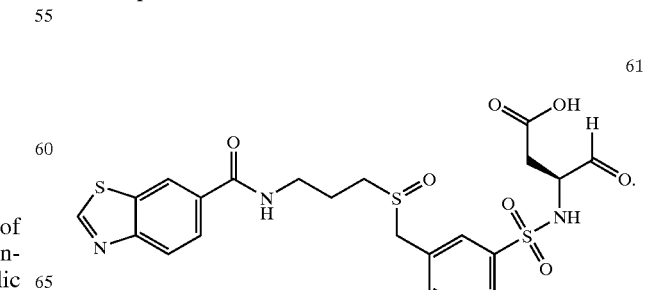

Compound 61 was prepared according to the procedure of Example 13a–j except substituting benzothiazole-6-carboxylic acid for 5-(methanesulphonyl)thiophene-2-carboxylic acid followed by the procedure of Example 15a–c. ES (+) MS: m/e=538 (M+1).

All references cited throughout the specification are expressly incorporated herein by reference. While the present invention has been described with reference to the specific embodiments thereof, it should be understood by those skilled in the art that various changes maybe made and equivalents may be substituted without departing from the true spirit and scope of the invention. In addition, many modifications may be made to adapt a particular situation, material, composition of matter, process, and the like. All such modifications are within the scope of the claims appended hereto.

What is claimed is:

1. A method comprising:
a) providing a target having a reactive nucleophile at or near a site of interest;
b) contacting the target with an extender thereby forming a target-extender complex wherein the extender comprises a first functionality that reacts with the nucleophile in the target to form a covalent bond and a second functionality that is capable of forming a disulfide bond, wherein the extender is of the formula:

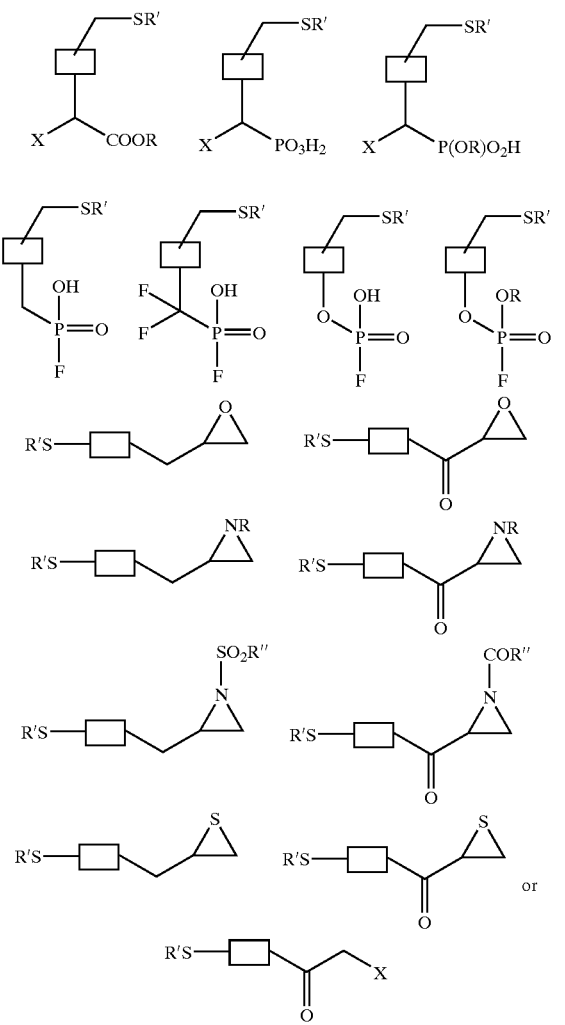

where R is unsubstituted $C_1$–$C_{20}$ aliphatic, substituted $C_1$–$C_{20}$ aliphatic, unsubstituted aryl, and substituted aryl; R' is H, —$SR^1$ wherein $R^1$ is unsubstituted $C_1$–$C_{10}$ aliphatic, substituted $C_1$–$C_{10}$ aliphatic, unsubstituted aryl, and substituted aryl; X is a leaving group, and the boxes in each formula represent a binding determinant;

c) contacting the target-extender complex with a candidate ligand that is capable of forming a disulfide bond with said target-extender complex;
d) forming a disulfide bond between the target-extender complex and the candidate ligand thereby forming a target-extender-ligand conjugate; and,
e) identifying the candidate ligand present in the target-extender-ligand conjugate.

2. The method of claim 1, wherein the candidate ligand present in the target-extender-ligand conjugate is identified by mass spectrometry.

3. The method of claim 1, wherein the candidate ligand present in the target-extender-ligand conjugate is identified using a labeled probe.

4. The method of claim 1, wherein the candidate ligand present in the target-extender-ligand conjugate is identified using a functional assay.

5. The method of claim 1, wherein the candidate ligand present in the target-extender-ligand conjugate is identified using chromatography.

6. The method of claim 1, wherein the candidate ligand present in the target-extender-ligand conjugate is identified using surface plasmon resonance.

7. A method comprising:
a) providing a target having a reactive nucleophile at or near a site of interest;
b) contacting the target with an extender thereby forming a target-extender complex wherein the extender comprises a first functionality that reacts with the nucleophile in the target to form a covalent bond and a second functionality that is capable of forming a disulfide bond, wherein the extender is of the formula:

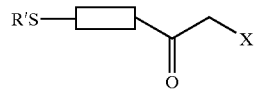

where R is unsubstituted $C_1$–$C_{20}$ aliphatic, substituted $C_1$–$C_{20}$ aliphatic, unsubstituted aryl, and substituted aryl; R' is H, —$SR^1$ wherein $R^1$ is unsubstituted $C_1$–$C_{10}$ aliphatic, substituted $C_1$–$C_{10}$ aliphatic, unsubstituted aryl, and substituted aryl; X is a leaving group, and the box in the formula represents a binding determinant;

c) contacting the target-extender complex with a candidate ligand that is capable of forming a disulfide bond with said target-extender complex;
d) forming a disulfide bond between the target-extender complex and the candidate ligand thereby forming a target-extender-ligand conjugate; and
e) identifying the candidate ligand present in the target-extender-ligand conjugate.

8. The method of claim 7, wherein the candidate ligand present in the target-extender-ligand conjugate is identified by mass spectrometry.

9. The method of claim 7, wherein the candidate ligand present in the target-extender-ligand conjugate is identified using a labeled probe.

10. The method of claim 7, wherein the candidate ligand present in the target-extender-ligand conjugate is identified using a functional assay.

11. The method of claim 7, wherein the candidate ligand present in the target-extender-ligand conjugate is identified using chromatography.

12. The method of claim 7, wherein the candidate ligand present in the target-extender-ligand conjugate is identified using surface plasmon resonance.

* * * * *